(12) United States Patent
Chetham et al.

(10) Patent No.: US 10,327,665 B2
(45) Date of Patent: *Jun. 25, 2019

(54) MONITORING SYSTEM

(71) Applicant: Impedimed Limited, Pinkenba, Queensland (AU)

(72) Inventors: Scott Chetham, Del Mar, CA (US); Andrew William Ward, The Gap (AU); James McFarlane Kennedy, St Lucia (AU)

(73) Assignee: Impedimed Limited, Pinkenba, Queensland (AU)

( * ) Notice: Subject to any disclaimer, the term of this patent is extended or adjusted under 35 U.S.C. 154(b) by 15 days.

This patent is subject to a terminal disclaimer.

(21) Appl. No.: 15/240,555

(22) Filed: Aug. 18, 2016

(65) Prior Publication Data

US 2016/0354008 A1 Dec. 8, 2016

Related U.S. Application Data

(63) Continuation of application No. 13/867,632, filed on Apr. 22, 2013, which is a continuation of application (Continued)

(30) Foreign Application Priority Data

Jul. 1, 2005 (AU) .................. 2005903510

(51) Int. Cl.
*A61B 5/053* (2006.01)
*A61B 5/00* (2006.01)

(52) U.S. Cl.
CPC .......... *A61B 5/0537* (2013.01); *A61B 5/0022* (2013.01); *A61B 5/053* (2013.01);
(Continued)

(58) Field of Classification Search
CPC ..... A61B 5/053; A61B 5/0531; A61B 5/0532; A61B 5/0533; A61B 5/0535; A61B 5/0537

See application file for complete search history.

(56) References Cited

U.S. PATENT DOCUMENTS

| | | | |
|---|---|---|---|
| 4,401,356 | A | 8/1983 | Bare |
| 4,407,288 | A | 10/1983 | Langer et al. |

(Continued)

FOREIGN PATENT DOCUMENTS

| | | |
|---|---|---|
| EP | 0357309 | 3/1990 |
| EP | 1219937 | 7/2002 |

(Continued)

OTHER PUBLICATIONS

Moissl, et al., Body fluid volume determination via body composition spectroscopy in health and disease, Physiol. Meas., 2006, vol. 27, pp. 921-933.

(Continued)

*Primary Examiner* — Adam J Eiseman
(74) *Attorney, Agent, or Firm* — Knobbe, Martens, Olson & Bear, LLP

(57) ABSTRACT

Apparatus for performing impedance measurements on a subject. The apparatus includes a first processing system for determining an impedance measurement procedure and determining instructions corresponding to the measurement procedure. A second processing system is provided for receiving the instructions, using the instructions to generate control signals, with the control signals being used to apply one or more signals to the subject. The second processing system then receives first data indicative of the one or more signals applied to the subject, second data indicative of one or more signals measured across the subject and performs at (Continued)

least preliminary processing of the first and second data to thereby allow impedance values to be determined.

32 Claims, 21 Drawing Sheets

Related U.S. Application Data

No. 11/993,340, filed as application No. PCT/AU2006/000922 on Jun. 30, 2006, now Pat. No. 8,548,580.

(60) Provisional application No. 60/697,100, filed on Jul. 7, 2005.

(52) U.S. Cl.
CPC .......... *A61B 5/6801* (2013.01); *A61B 5/7203* (2013.01); *A61B 5/7221* (2013.01); *A61B 5/7225* (2013.01); *A61B 5/7257* (2013.01); *A61B 5/7278* (2013.01); *A61B 5/746* (2013.01); *A61B 5/7475* (2013.01); *A61B 5/7495* (2013.01); *A61B 2562/08* (2013.01); *A61B 2562/166* (2013.01)

(56) References Cited

U.S. PATENT DOCUMENTS

| | | | |
|---|---|---|---|
| 4,695,955 A | 9/1987 | Faisandier | |
| 4,793,362 A | 12/1988 | Tedner | |
| 4,832,608 A | 5/1989 | Kroll | |
| 4,836,214 A | 6/1989 | Sramek et al. | |
| 5,372,141 A * | 12/1994 | Gallup | A61B 5/0002 600/547 |
| 5,626,135 A | 5/1997 | Sanfilippo | |
| 5,679,022 A | 10/1997 | Cappa et al. | |
| 5,800,350 A | 9/1998 | Coppleson et al. | |
| 5,906,614 A | 5/1999 | Stern et al. | |
| 6,011,992 A | 1/2000 | Hubbard et al. | |
| 6,026,323 A | 2/2000 | Skladnev et al. | |
| 6,142,949 A | 11/2000 | Ubby | |
| 6,151,520 A | 11/2000 | Combs | |
| 6,228,033 B1 | 5/2001 | Kööbi | |
| 6,256,532 B1 | 7/2001 | Cha | |
| 6,292,690 B1 | 9/2001 | Petrucelli et al. | |
| 6,633,777 B2 | 10/2003 | Szopinski | |
| 6,884,214 B2 | 4/2005 | Itagaki | |
| 6,906,533 B1 | 6/2005 | Yoshida | |
| 8,548,580 B2 * | 10/2013 | Chetham | A61B 5/053 600/547 |
| 2001/0025139 A1 | 9/2001 | Pearlman | |
| 2002/0072682 A1 | 6/2002 | Hopman et al. | |
| 2002/0109621 A1 | 8/2002 | Khair et al. | |
| 2002/0193689 A1 * | 12/2002 | Bernstein | A61B 5/029 600/454 |
| 2003/0004403 A1 | 1/2003 | Drinan et al. | |
| 2003/0004433 A1 | 1/2003 | Hirschman | |
| 2003/0105410 A1 | 6/2003 | Pearlman | |
| 2004/0073127 A1 | 4/2004 | Istvan et al. | |
| 2004/0236202 A1 | 11/2004 | Burton | |
| 2004/0260167 A1 | 12/2004 | Leonhardt et al. | |
| 2004/0267344 A1 | 12/2004 | Stett et al. | |
| 2005/0020935 A1 | 1/2005 | Helzel et al. | |
| 2005/0049474 A1 | 3/2005 | Kellogg et al. | |
| 2005/0101875 A1 * | 5/2005 | Semler | A61B 5/04085 600/509 |
| 2005/0137480 A1 | 6/2005 | Alt et al. | |
| 2006/0085049 A1 * | 4/2006 | Cory | A61B 5/0536 607/48 |
| 2006/0264775 A1 | 11/2006 | Mills et al. | |

FOREIGN PATENT DOCUMENTS

| | | |
|---|---|---|
| JP | 61-2563 | 1/1986 |
| JP | 04-096733 | 3/1992 |
| JP | 10-080406 | 3/1998 |
| JP | 11-513592 | 11/1999 |
| JP | 2001-224568 | 8/2001 |
| JP | 2002-330938 | 11/2002 |
| JP | 2003-116803 | 4/2003 |
| JP | 2004-061251 | 2/2004 |
| JP | 2005-505388 | 2/2005 |
| JP | 2005-143786 | 6/2005 |
| WO | WO 94-10922 | 5/1994 |
| WO | WO 96-11631 | 4/1996 |
| WO | WO 97-014358 | 4/1997 |
| WO | WO 97-43000 | 11/1997 |
| WO | WO 98-54792 | 12/1998 |
| WO | WO 00-78213 | 12/2000 |
| WO | WO 01-78831 | 10/2001 |
| WO | WO 2002-100267 | 12/2002 |
| WO | WO 2004-006764 | 1/2004 |
| WO | WO 2004-006764 | 1/2004 |
| WO | WO 2004-043252 | 5/2004 |
| WO | WO 2004-112563 | 12/2004 |
| WO | WO 2005-018432 | 6/2005 |
| WO | WO 2005-122888 | 12/2005 |

OTHER PUBLICATIONS

Wang, et al., Hydration of fat-free body mass: new physiological modeling approach, Am. J. Physiol. Endocrinol. Metab., 1999, vol. 276, pp. E995-E1003.

* cited by examiner

MONITORING SYSTEM

CROSS-REFERENCE TO RELATED APPLICATIONS

The present application is a continuation of U.S. application Ser. No. 13/867,632, filed Apr. 22, 2013, which is a continuation of U.S. application Ser. No. 11/993,340, filed Dec. 14, 2010, which is a U.S. National Phase under 35 U.S.C. 371 of the International Patent Application No. PCT/AU06/000922, filed Jun. 30, 2006, and published in English on Jan. 11, 2007 as WO 2007/002991, which claims the benefit of U.S. Provisional Application No. 60/697,100, filed Jul. 7, 2005, and Australian Application No. 2005903510, filed Jul. 1, 2005.

BACKGROUND OF THE INVENTION

The present invention relates to a method and apparatus for monitoring biological parameters, and in particular to apparatus for making impedance measurements.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

One existing technique for determining biological parameters relating to a subject, such as cardiac function, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema.

Accordingly, complex signal processing is required to ensure measurements can be interpreted.

Typically devices for achieving this utilise custom hardware configurations that are application specific. As a result, the devices can typically only be used in a limited range of circumstances.

SUMMARY OF THE PRESENT INVENTION

In a first broad form the present invention provides apparatus for performing impedance measurements on a subject, the apparatus including:
a) a first processing system for:
  i) determining an impedance measurement procedure; and,
  ii) selecting instructions corresponding to the measurement procedure; and,
b) a second processing system for:
  i) generating, using the instructions, control signals, the control signals being used to apply one or more signals to the subject;
  ii) receiving an indication of the one or more signals applied to the subject;
  iii) receiving an indication of one or more signals measured across the subject;
  iv) performing, using the instructions, at least preliminary processing of the indications to thereby allow impedance values to be determined.

Typically the method includes, transferring the instructions from the first processing system to the second processing system.

Typically the method includes, selecting the instructions using configuration data.

Typically the method includes, receiving the configuration data from a remote processing system.

Typically the instructions are in the form of at least one of:
a) firmware; and,
b) embedded systems.

Typically the second processing system is an FPGA.

Typically the apparatus includes an input device, and wherein the first processing system is coupled to the input device to thereby determine the impedance measurement procedure in accordance with input commands from an operator.

Typically the first processing system includes a store for storing at least one profile, the at least one profile representing a predetermined impedance measurement procedure.

Typically the control signals represent a sequence of predetermined electrical signals, the sequence being dependent on the selected impedance measurement type.

Typically the apparatus includes:
a) a current ADC for:
  i) receiving signals from a current circuit; and,
  ii) providing the indication of the one or more signals applied to the subject to the second processing system; and,
b) a voltage ADC for:
  i) receiving signals from a voltage circuit; and,
  ii) providing the indication of the one or more signals measured from the subject to the second processing system.

Typically the apparatus includes at least one buffer circuit for:
a) receiving voltage signals from a voltage electrode;
b) filtering and amplifying the voltage signals; and,
c) transferring the filtered and amplified voltage signals to the voltage ADC via a differential amplifier.

Typically the apparatus includes a current source circuit for:
a) receiving one or more control signals;
b) filtering and amplifying the control signals to thereby generate one or more current signals;
c) applying the current signals to a current electrode; and,
d) transferring an indication of the applied signals to the current ADC.

Typically the apparatus includes a control signal DAC for:
a) receiving the control signals from the second processing system; and,
b) providing analogue control signals to a current circuit to thereby cause one or more current signals to be applied to the subject in accordance with the control signals.

Typically the second processing system is formed from first and second processing system portions, the first and second processing system portions being electrically isolated to thereby electrically isolate the subject from the first processing system.

Typically the apparatus includes:
a) a measuring device including at least the first processing system; and,
b) one or more subject units, each subject unit including at least part of the second processing system.

Typically the apparatus includes at least two current electrodes for applying current signals to the subject, and a switch connected to the current electrodes for discharging the subject prior to measuring the induced voltage.

Typically the apparatus includes a housing having:
a) a display;
b) a first circuit board for mounting at least one of the processing systems;
c) a second circuit board for mounting at least one of an ADC and a DAC; and,
d) a third circuit board for mounting a power supply.

Typically the housing is formed from at least one of a mu-metal and aluminium with added magnesium, to thereby provide electrical/magnetic shielding.

Typically the apparatus includes multiple channels, each channel being for performing impedance measurements using a respective set of electrodes.

Typically the apparatus is for:
a) determining an electrode identifier associated with at least one electrode provided on the subject;
b) determining, using the electrode identifier, an electrode position indicative of the position of the at least one electrode on the subject; and,
c) performing at least one impedance measurement using the electrode position.

Typically the apparatus is for:
a) determining a parameter associated with at least one electrode lead; and,
b) causing at least one impedance measurement to be performed using the determined parameter.

Typically the apparatus is for:
a) receiving configuration data, the configuration data being indicative of at least one feature;
b) determining, using the configuration data, instructions representing the at least one feature; and,
c) causing, using the instructions, at least one of:
   i) at least one impedance measurement to be performed; and,
   ii) at least one impedance measurement to be analysed.

Typically the apparatus is for:
a) causing a first signal to be applied to the subject;
b) determining at least one parameter relating to at least one second signal measured across the subject;
c) comparing the at least one parameter to at least one threshold; and,
d) depending on the results of the comparison, selectively repeating steps (a) to (d) using a first signal having an increased magnitude.

In a second broad form the present invention provides a method of performing impedance measurements on a subject, the method including:
a) using a first processing system for:
   i) determining an impedance measurement procedure; and,
   ii) selecting instructions corresponding to the measurement procedure; and,
b) using a second processing system for:
   i) generating, using the instructions, control signals, the control signals being used to apply one or more signals to the subject;
   ii) receiving an indication of the one or more signals applied to the subject;
   iii) receiving an indication of one or more signals measured across the subject;
   iv) performing, using the instructions, at least preliminary processing of the first and second data to thereby allow impedance values to be determined.

In a third broad form the present invention provides a method of diagnosing conditions in a subject, the method including, in a processing system:
a) using a first processing system for:
   i) determining an impedance measurement procedure; and,
   ii) selecting instructions corresponding to the measurement procedure; and,
b) using a second processing system for:
   i) generating, using the instructions, control signals, the control signals being used to apply one or more signals to the subject;
   ii) receiving an indication of the one or more signals applied to the subject;
   iii) receiving an indication of one or more signals measured across the subject;
   iv) performing, using the instructions, at least preliminary processing of the first and second data to thereby allow impedance values to be determined.

In a fourth broad form the present invention provides apparatus for connecting measurement apparatus to an electrode, the apparatus including:
a) a housing having a connector for coupling the housing to an electrode; and,
b) a circuit mounted in the housing, the circuit being electrically coupled to the electrode using the connector, and being coupled to a lead, the circuit being for at least one of:
   i) generating predetermined electrical signals in accordance with control signals received from the measurement apparatus;
   ii) providing an indication of electrical signals applied to the electrode; and,
   iii) providing an indication of electrical signals measured at the electrode.

Typically the circuit is provided on a circuit board having an electrical contact, and wherein in use the connector urges at least part of the electrode into abutment with the electrical contact.

Typically the connector includes a biased arm.

Typically the circuit includes a buffer circuit for:
a) sensing voltage signals at the electrode;
b) filtering and amplifying the voltage signals; and,
c) transferring the filtered and amplified voltage signals to the measurement apparatus.

Typically the circuit includes a current source circuit for:
a) receiving one or more control signals;
b) filtering and amplifying the control signals to thereby generate one or more current signals;
c) applying the current signals to the electrode pad; and,
d) transferring an indication of the applied signals to the measurement apparatus.

Typically the apparatus further comprises an electrode, the electrode including:
a) an electrode substrate; and,
b) a conductive material for electrically coupling the electrode to the subject.

Typically the electrode substrate is electrically conductive, and wherein in use the connector couples the circuit to the electrode substrate.

Typically the housing includes curved edges.

Typically the housing is formed from a material that, at least one of:
a) has a low coefficient of friction; and,
b) is resilient.

In a fifth broad form the present invention provides a method of performing impedance measurements on a subject, the method including, in a processing system:
  a) determining an encoded value associated with at least one electrode lead; and,
  b) causing at least one impedance measurement to be performed using the encoded value.

Typically the encoded value is used for calibration.

Typically the encoded value is determined from a resistance value.

Typically the encoded value is indicative of an identity of the lead.

Typically the method includes, in the processing system, controlling the current applied to the subject using the determined resistance.

Typically the encoded value is a lead identifier, and wherein the method includes, in the processing system:
  a) determining, using the lead identifier, an impedance measurement procedure; and,
  b) causing the determined impedance measurement procedure to be performed.

Typically the method includes, in the processing system:
  a) comparing the determined identity to one or more predetermined identities; and,
  b) determining the impedance of the subject in response to a successful comparison.

Typically the method includes, in the processing system:
  a) determining the lead identifier associated with the at least one electrode lead;
  b) determining, using the lead identifier, a lead usage;
  c) comparing the lead usage to a threshold; and,
  d) in accordance with the results of the comparison, at least one of:
    i) generating an alert;
    ii) terminating an impedance measurement procedure; and,
    iii) performing an impedance measurement procedure.

Typically the method includes, in the processing system, at least one of:
  a) processing electrical signals measured from the subject to thereby determine one or more impedance values; and,
  b) processing determined impedance values.

Typically the encoded value is stored in a store.

In a sixth broad form the present invention provides apparatus for performing impedance measurements on a subject, the apparatus including:
  a) at least one lead for connecting to electrodes coupled to the subject, the at least one lead including an encoded value; and,
  b) a processing system coupled to the at least one lead for:
    i) determining the encoded value; and,
  c) causing at least one impedance measurement to be performed using the encoded value.

In a seventh broad form the present invention provides a method of performing impedance measurements on a subject, the method including, in a processing system:
  a) determining an electrode identifier associated with at least one electrode provided on the subject;
  b) determining, using the electrode identifier, an electrode position indicative of the position of the at least one electrode on the subject; and,
  c) causing at least one impedance measurement to be performed using the electrode position.

Typically the impedance measurement is performed using at least four electrodes, each having a respective identifier, and wherein the method includes, in the processing system:
  a) determining an electrode identifier for each electrode;
  b) determining, using each electrode identifier, an electrode position for each electrode; and,
  c) performing at least one impedance measurement using the electrode positions.

Typically the method includes, in the processing system:
  a) causing signals to be applied to at least two of the electrodes in accordance with the determined electrode positions; and,
  b) causing signals to be measured from at least two of the electrodes in accordance with the determined electrode positions.

Typically the method includes, in the processing system, determining the electrode identifier for an electrode by selectively measuring the conductivity between one or more contacts provided on the electrode.

Typically the processing system is coupled to a signal generator and a sensor, and wherein the method includes, in the processing system:
  a) selectively interconnecting the signal generator and at least two electrode leads, to thereby allow signals to be applied to the subject; and,
  b) selectively interconnecting the sensor at least two electrode leads to thereby allow a signal to be measured from the subject.

Typically the method includes, in the processing system controlling a multiplexer to thereby selectively interconnect the leads and at least one of the signal generator and the sensor.

Typically the at least one electrode includes visual indicia indicative of the position of the at least one electrode on the subject.

In an eighth broad form the present invention provides apparatus for performing impedance measurements on a subject, the apparatus including a processing system for:
  a) determining an electrode identifier associated with at least one electrode provided on the subject;
  b) determining, using the electrode identifier, an electrode position indicative of the position of the at least one electrode on the subject; and,
  c) causing at least one impedance measurement to be performed using the electrode position.

In a ninth broad form the present invention provides a method for configuring a measuring device for measuring the impedance of a subject, the method including, in a processing system:
  a) receiving configuration data, the configuration data being indicative of at least one feature;
  b) determining, using the configuration data, instructions representing the at least one feature; and,
  c) causing, at least in part using the instructions, at least one of:
    i) impedance measurements to be performed; and,
    ii) analysis of impedance measurements.

Typically the configuration data includes the instructions.

Typically the method includes, in the processing system:
  a) determining an indication of the at least one feature using the configuration data; and,
  b) determining the instructions using the indication of the at least one feature.

Typically the method includes, in the processing system, decrypting the received configuration data.

Typically the method includes, in the processing system:
  a) determining a device identifier associated with the measuring device;
  b) determining, using the device identifier, a key; and, c) decrypting the received configuration data using the key.

Typically the processing system includes first and second processing systems, and wherein the method includes:
  a) in the first processing system, selecting the instructions using the configuration data; and,
  b) in the second processing system, generating the control signals using selected instructions.

Typically the method includes, in the processing first system, at least one of:
  a) transferring the instructions to the second processing system; and,
  b) causing the second processing system to access the instructions from a store.

Typically the method includes, in the processing system, receiving the configuration data from at least one of a computer system and a communications network.

Typically the method includes, in the processing system:
  a) determining if a feature selected by a user is available;
  b) if the feature is not available, determining if the user wishes to enable the feature; and,
  c) if the user wishes to enable the feature, causing configuration data to be received.

Typically the method includes, in the processing system:
  a) causing the user to provide a payment to a device provider; and,
  b) receiving the configuration data in response to payment.

In a tenth broad form the present invention provides apparatus for configuring a measuring device for measuring the impedance of a subject, the apparatus including a processing system for:
  a) receiving configuration data, the configuration data being indicative of at least one feature;
  b) determining, using the configuration data, instructions representing the at least one feature; and,
  c) causing, at least in part using the instructions, at least one of:
    i) impedance measurements to be performed; and,
    ii) analysis of impedance measurements.

In an eleventh broad form the present invention provides a method for configuring a measuring device for measuring the impedance of a subject, the method including, in a computer system:
  a) determining configuration data required for a measuring device, the configuration data being indicative of at least one feature; and,
  b) causing the configuration data to be received by a processing system in the measuring device, the processing system being responsive to the configuration data to configure the measuring device to allow the at least one feature to be used.

Typically the method includes, in the computer system:
  a) determining a device identifier, the device identifier being associated with the measuring device to be configured; and,
  b) using the device identifier to at least one of:
    i) transfer the configuration data to the measuring device; and,
    ii) encrypt the configuration data.

Typically the method includes, in the computer system, determining the configuration data is required in response to at least one of:
  a) payment made by a user of the measuring device; and,
  b) approval of the feature.

Typically the method includes, in the computer system:
  a) determining regulatory approval of the at least one feature in at least one region;
  b) determining at least one measuring device in the at least one region; and,
  c) configuring the at least one measuring device.

In a twelfth broad form the present invention provides apparatus for configuring a measuring device for measuring the impedance of a subject, the method including, in a computer system:
  a) determining configuration data required for a measuring device, the configuration data being indicative of at least one feature; and,
  b) causing the configuration data to be received by a processing system in the measuring device, the processing system being responsive to the configuration data to configure the measuring device to allow the at least one feature to be used.

In a thirteenth broad form the present invention provides a method of performing impedance measurements on a subject, wherein the method includes, in a processing system:
  a) causing a first signal to be applied to the subject;
  b) determining at least one parameter relating to at least one second signal measured across the subject;
  c) comparing the at least one parameter to at least one threshold; and,
  d) depending on the results of the comparison, selectively repeating steps (a) to (d) using a first signal having an increased magnitude.

Typically the method includes, in the processing system:
  a) determining an animal type of the subject; and,
  b) selecting the threshold in accordance with the animal type.

Typically the threshold is indicative of at least one of:
  a) a minimum second signal magnitude; and,
  b) a minimum signal to noise ratio for the second signal.

Typically the method includes, in the processing system:
  a) determining at least one parameter relating to the at least one first signal;
  b) comparing the at least one parameter to at least one threshold; and,
  c) selectively terminating impedance measurements depending on the results of the comparison.

Typically the threshold is indicative of a maximum first signal magnitude.

In a fourteenth broad form the present invention provides apparatus for performing impedance measurements on a subject, wherein the apparatus includes a processing system for:
  a) causing a first signal to be applied to the subject;
  b) determining at least one parameter relating to at least one second signal measured across the subject;
  c) comparing the at least one parameter to at least one threshold; and,
  d) depending on the results of the comparison, selectively repeating steps (a) to (d) using a first signal having an increased magnitude.

Typically the apparatus further includes a variable magnitude current supply.

In another broad form the present invention provides a method of providing an electrode for use in impedance measurement procedures, the method including:

a) providing on a substrate:
  i) a number of electrically conductive contact pads; and,
  ii) a corresponding number of electrically conductive tracks, each track extending from an edge of the substrate to a respective contact pad;
b) applying an insulating layer to the substrate, the insulating layer including a number of apertures, and being positioned to thereby overlay the tracks with at least a portion of each pad contact aligned with a respective aperture; and,
c) providing an electrically conductive medium in the apertures.

Typically the electrically conductive medium is formed from a conductive gel.

Typically the conductive gel is silver/silver chloride gel.

Typically the method includes, providing a covering layer on the insulating layer to thereby cover the electrically conductive medium.

Typically the insulating layer has an adhesive surface that releasably engages the covering layer.

Typically the substrate is an elongate substrate, and wherein the method includes aligning the pad contacts along the length of the substrate.

Typically the method includes providing the tracks and contact pads using at least one of:
  a) screen printing;
  b) inkjet printing; and,
  c) vapour deposition.

Typically the tracks and contact pads are formed from silver.

Typically the method includes forming the substrate by:
  a) overlaying a plastic polymer with a shielding material; and,
  b) covering the shielding material with an insulating material.

In a fifteenth broad form the present invention provides an electrode for use in impedance measurement procedures, the electrode including:
  a) a substrate having provided thereon:
    i) a number of electrically conductive contact pads; and,
    ii) a corresponding number of electrically conductive tracks, each track extending from an edge of the substrate to a respective contact pad;
  b) an insulating layer provided on the substrate, the insulating layer including a number of apertures, and being positioned to thereby overlay the tracks with at least a portion of each pad contact aligned with a respective aperture; and,
  c) an electrically conductive medium provided in the apertures.

In a sixteenth broad form the present invention provides a method for use in diagnosing conditions in a subject, the method including, in a processing system:
  a) determining an encoded value associated with at least one electrode lead; and,
  b) causing at least one impedance measurement to be performed using the encoded value.

In a seventeenth broad form the present invention provides a method for use in diagnosing conditions in a subject, the method including, in a processing system:
  a) determining an electrode identifier associated with at least one electrode provided on the subject;
  b) determining, using the electrode identifier, an electrode position indicative of the position of the at least one electrode on the subject; and,
  c) causing at least one impedance measurement to be performed using the electrode position.

In an eighteenth broad form the present invention provides a method for use in diagnosing conditions in a subject, the method including, in a processing system:
  a) receiving configuration data, the configuration data being indicative of at least one feature;
  b) determining, using the configuration data, instructions representing the at least one feature; and,
  c) causing the measuring device to perform, using the instructions, at least one of:
    i) impedance measurements; and,
    ii) analysis of impedance measurements.

In a nineteenth broad form the present invention provides a method for use in diagnosing conditions in a subject, the method including, in a processing system:
  a) determining configuration data required for a measuring device, the configuration data being indicative of at least one feature; and,
  b) causing the configuration data to be received by a processing system in the measuring device, the processing system being responsive to the configuration data to configure the measuring device to allow the at least one feature to be used.

In a twentieth broad form the present invention provides a method for use in diagnosing conditions in a subject, the method including, in a processing system:
  a) causing a first signal to be applied to the subject;
  b) determining at least one parameter relating to at least one second signal measured across the subject;
  c) comparing the at least one parameter to at least one threshold; and,
  d) depending on the results of the comparison, selectively repeating steps (a) to (d) using a first signal having an increased magnitude.

It will be appreciated that the broad forms of the invention may be used individual or in combination, and may be used for diagnosis of the presence, absence or degree of a range of conditions and illnesses, including, but not limited to oedema, pulmonary oedema, lymphodema, body composition, cardiac function, and the like.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
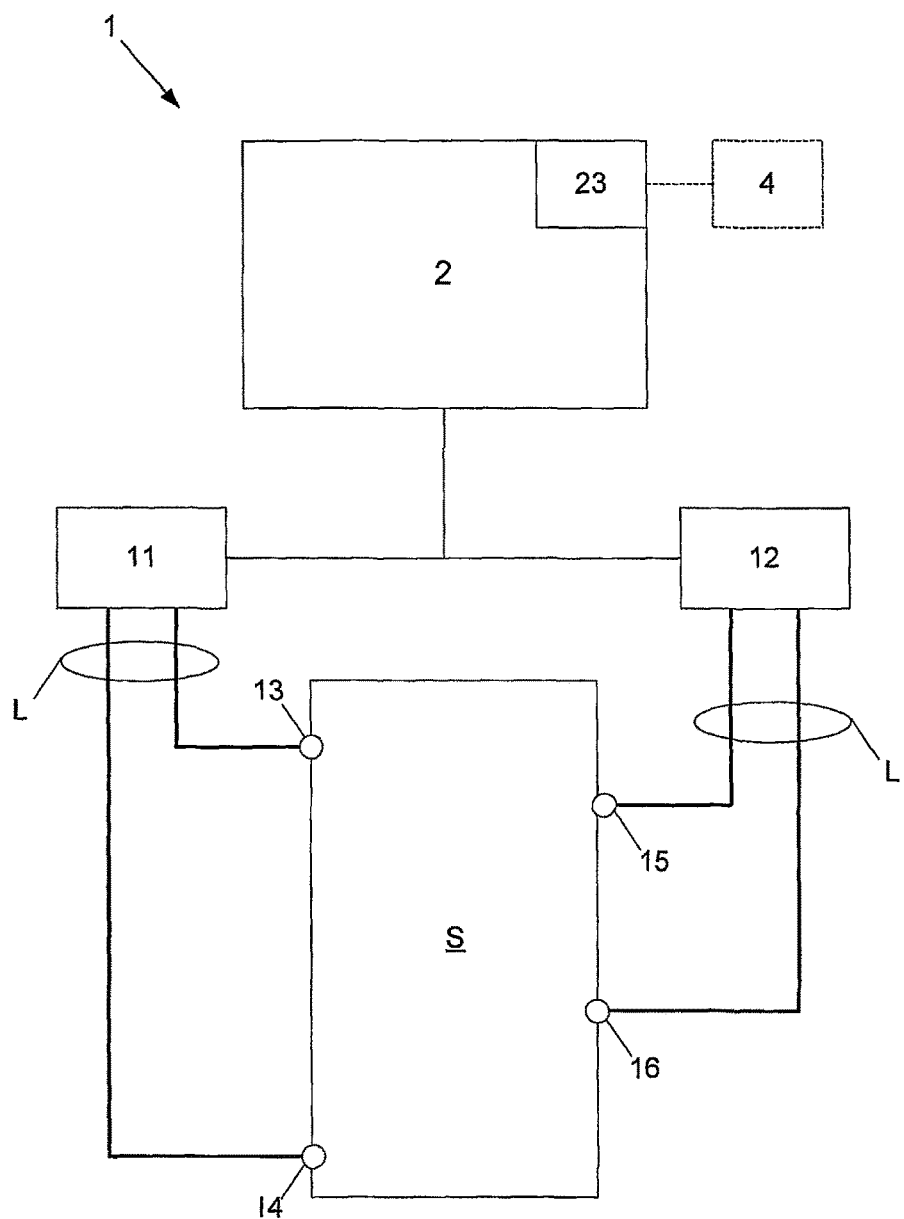
FIG. 1 is a schematic of an example of impedance determination apparatus.

An example of apparatus suitable for performing an analysis of a subject's bioelectric impedance will now be described with reference to FIG. 1.

As shown the apparatus includes a measuring device 1 including a processing system 2 coupled to a signal generator 11 and a sensor 12. In use the signal generator 11 and the sensor 12 are coupled to respective electrodes 13, 14, 15, 16, provided on a subject S, via leads L, as shown. An optional external interface 23 can be used to couple the measuring device 1 to one or more peripheral devices 4, such as an external database or computer system, barcode scanner, or the like.

In use, the processing system 2 is adapted to generate control signals, which causes the signal generator 11 to generate one or more alternating signals, such as voltage or current signals, which can be applied to a subject S, via the electrodes 13, 14. The sensor 12 then determines the voltage across or current through the subject S, using the electrodes 15, 16 and transfers appropriate signals to the processing system 2.

Accordingly, it will be appreciated that the processing system 2 may be any form of processing system which is suitable for generating appropriate control signals and interpreting an indication of the measured signals to thereby determine the subject's bioelectrical impedance, and optionally determine other information such as the cardiac parameters, presence absence or degree of oedema, or the like.

The processing system 2 may therefore be a suitably programmed computer system, such as a laptop, desktop, PDA, smart phone or the like. Alternatively the processing system 2 may be formed from specialised hardware. Similarly, the I/O device may be of any suitable form such as a touch screen, a keypad and display, or the like.

It will be appreciated that the processing system 2, the signal generator 11 and the sensor 12 may be integrated into a common housing and therefore form an integrated device. Alternatively, the processing system 2 may be connected to the signal generator 11 and the sensor 12 via wired or wireless connections. This allows the processing system 2 to be provided remotely to the signal generator 11 and the sensor 12. Thus, the signal generator 11 and the sensor 12 may be provided in a unit near, or worn by the subject S, whilst the processing system 2 is situated remotely to the subject S.

In one example, the outer pair of electrodes 13, 14 are placed on the thoracic and neck region of the subject S. However, this depends on the nature of the analysis being performed. Thus, for example, whilst this electrode arrangement is suitable for cardiac function analysis, in lymphoedema, the electrodes would typically be positioned on the limbs, as required.

Once the electrodes are positioned, an alternating signal is applied to the subject S. This may be performed either by applying an alternating signal at a plurality of frequencies simultaneously, or by applying a number of alternating signals at different frequencies sequentially. The frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between an inner pair of electrodes 15, 16. The acquired signal and the measured signal will be a superposition of potentials generated by the human body, such as the ECG, and potentials generated by the applied current.

Optionally the distance between the inner pair of electrodes may be measured and recorded. Similarly, other parameters relating to the subject may be recorded, such as the height, weight, age, sex, health status, any interventions and the date and time on which they occurred. Other information, such as current medication, may also be recorded.

To assist accurate measurement of the impedance, buffer circuits may be placed in connectors that are used to connect the voltage sensing electrodes 15, 16 to the leads L. This ensures accurate sensing of the voltage response of the subject S, and in particular helps eliminate contributions to the measured voltage due to the response of the leads L, and reduce signal loss.

This in turn greatly reduces artefacts caused by movement of the leads L, which is particularly important during dialysis as sessions usually last for several hours and the subject will move around and change positions during this time.

A further option is for the voltage to be measured differentially, meaning that the sensor used to measure the potential at each electrode 15, 16 only needs to measure half of the potential as compared to a single ended system.

The current measurement system may also have buffers placed in the connectors between the electrodes 13, 14 and the leads L. In one example, current can also be driven or sourced through the subject S symmetrically, which again greatly reduced the parasitic capacitances by halving the common-mode current. Another particular advantage of using a symmetrical system is that the micro-electronics built into the connectors for each electrode 13, 14 also removes parasitic capacitances that arise when the subject S, and hence the leads L move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 2:
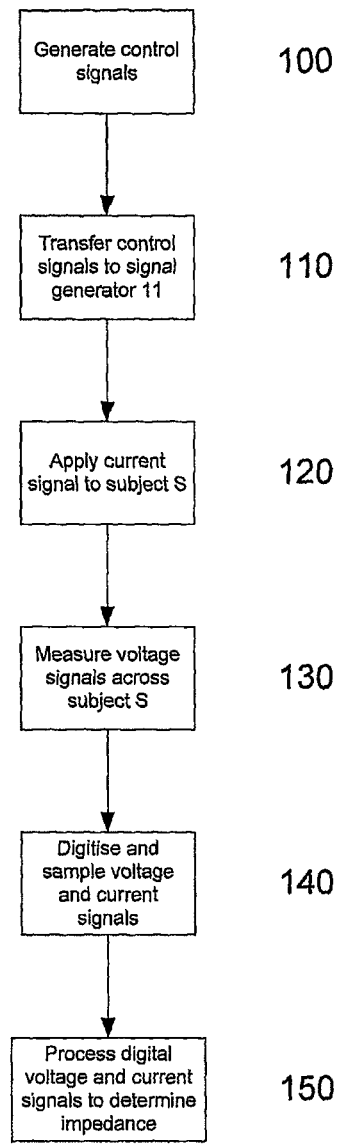
FIG. 2 is a flowchart of an example of a process for performing impedance determination.

An example of the operation of the apparatus for performing impedance analysis will now be described with reference to FIG. 2.

At step 100, the processing system 2 operates to generate control signals which are provided to the signal generator 11 at step 110, thereby causing the signal generator to apply an alternating current signal to the subject S, at step 120. Typically the signal is applied at each of a number of frequencies f, to allow multiple frequency analysis to be performed.

At step 130 the sensor 12 senses voltage signals across the subject S. At step 140 the measuring device, operates to digitise and sample the voltage and current signals across the subject S, allowing these to be used to determine instantaneous impedance values for the subject S at step 150.

Figure 3:
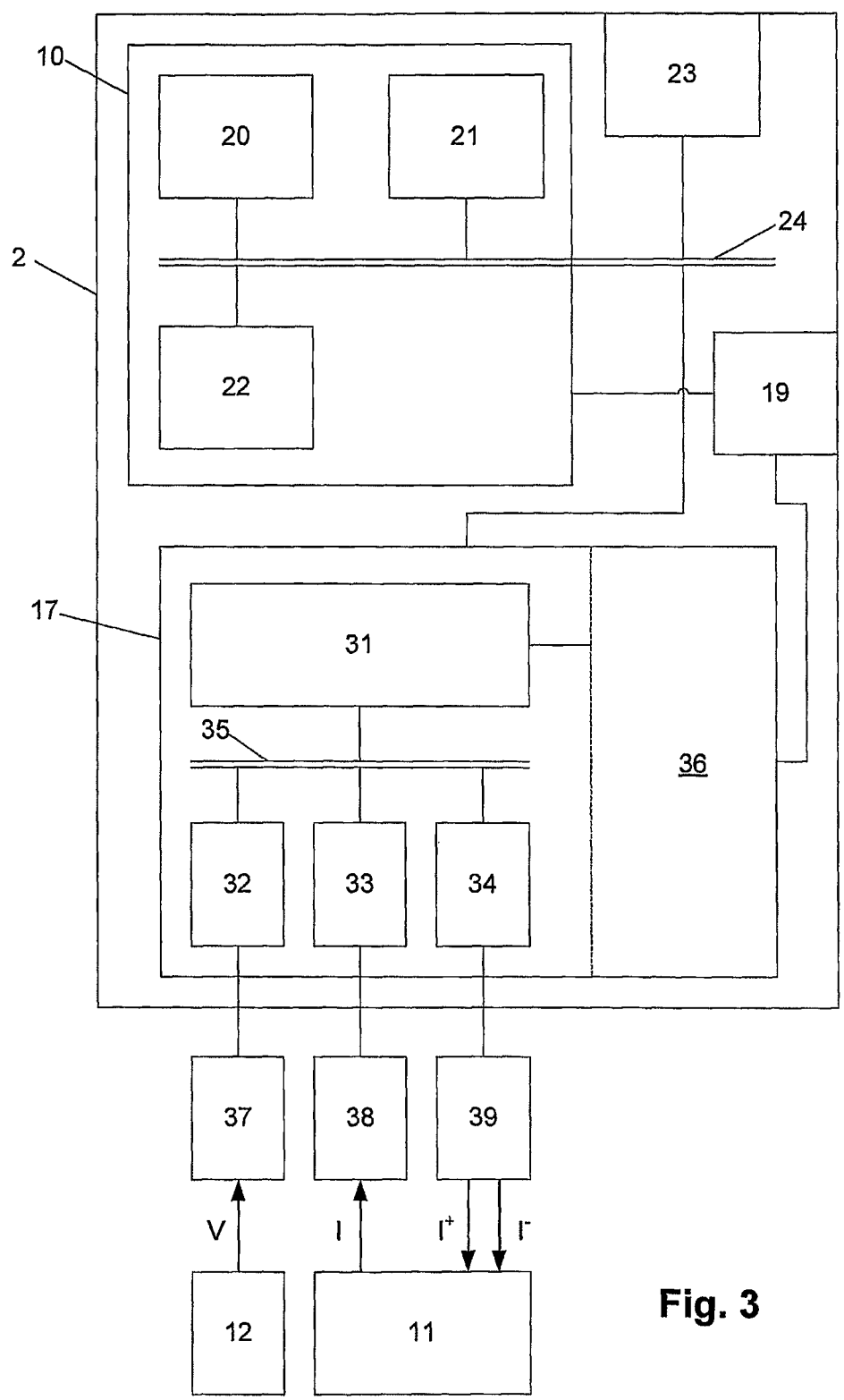
FIG. 3 is a schematic of a second example impedance determination apparatus.

A specific example of the apparatus will now be described in more detail with respect to FIG. 3.

In this example, the processing system 2 includes a first processing system 10 having a processor 20, a memory 21, an input/output (I/O) device 22, and an external interface 23, coupled together via a bus 24. The processing system 2 also includes a second processing system 17, in the form of a processing module. A controller 19, such as a micrologic controller, may also be provided to control activation of the first and second processing systems 10, 17.

In use, the first processing system 10 controls the operation of the second processing system 17 to allow different impedance measurement procedures to be implemented, whilst the second processing system 17 performs specific processing tasks, to thereby reduce processing requirements on the first processing system 10.

Thus, the generation of the control signals, as well as the processing to determine instantaneous impedance values is performed by the second processing system 17, which may therefore be formed from custom hardware, or the like. In one particular example, the second processing system 17 is formed from a Field Programmable Gate Array (FPGA), although any suitable processing module, such as a magnetologic module, may be used.

The operation of the first and second processing systems 10, 17, and the controller 19 is typically controlled using one or more sets of appropriate instructions. These could be in any suitable form, and may therefore include, software, firmware, embedded systems, or the like.

The controller 19 typically operates to detect activation of the measuring device through the use of an on/off switch (not shown). Once the controller detects device activation, the controller 19 executes predefined instructions, which in turn causes activation of the first and second processing systems 10, 17, including controlling the supply of power to the processing systems as required.

The first processing system 10 can then operate to control the instructions, such as the firmware, implemented by the second processing system 17, which in turn alters the operation of the second processing system 17. Additionally, the first processing system 10 can operate to analyse impedance determined by the second processing system 17, to allow biological parameters to be determined. Accordingly, the first processing system 10 may be formed from custom hardware or the like, executing appropriate applications software to allow the processes described in more detail below to be implemented.

It will be appreciated that this division of processing between the first processing system 10, and the second processing system 17, is not essential, but there are a number of benefits that will become apparent from the remaining description.

In this example, the second processing system 17 includes a PCI bridge 31 coupled to programmable module 36 and a bus 35, as shown. The bus 35 is in turn coupled to processing modules 32, 33, 34, which interface with ADCs (Analogue to Digital Converters) 37, 38, and a DAC (Digital to Analogue Converter) 39, respectively.

The programmable module 36 is formed from programmable hardware, the operation of which is controlled using the instructions, which are typically downloaded from the first processing system 10. The firmware that specifies the configuration of hardware 36 may reside in flash memory (not shown), in the memory 21, or may be downloaded from an external source via the external interface 23.

Alternatively, the instructions may be stored within inbuilt memory on the second processing system 17. In this example, the first processing system 10 typically selects firmware for implementation, before causing this to be implemented by the second processing system 17. This may be achieved to allow selective activation of functions encoded within the firmware, and can be performed for example using configuration data, such as a configuration file, or instructions representing applications software or firmware, or the like, as will be described in more detail below.

In either case, this allows the first processing system 10 to be used to control operation of the second processing system 17 to allow predetermined current sequences to be applied to the subject S. Thus, for example, different firmware would be utilised if the current signal is to be used to analyse the impedance at a number of frequencies simultaneously, for example, by using a current signal formed from a number of superposed frequencies, as compared to the use of current signals applied at different frequencies sequentially.

Figure 4:
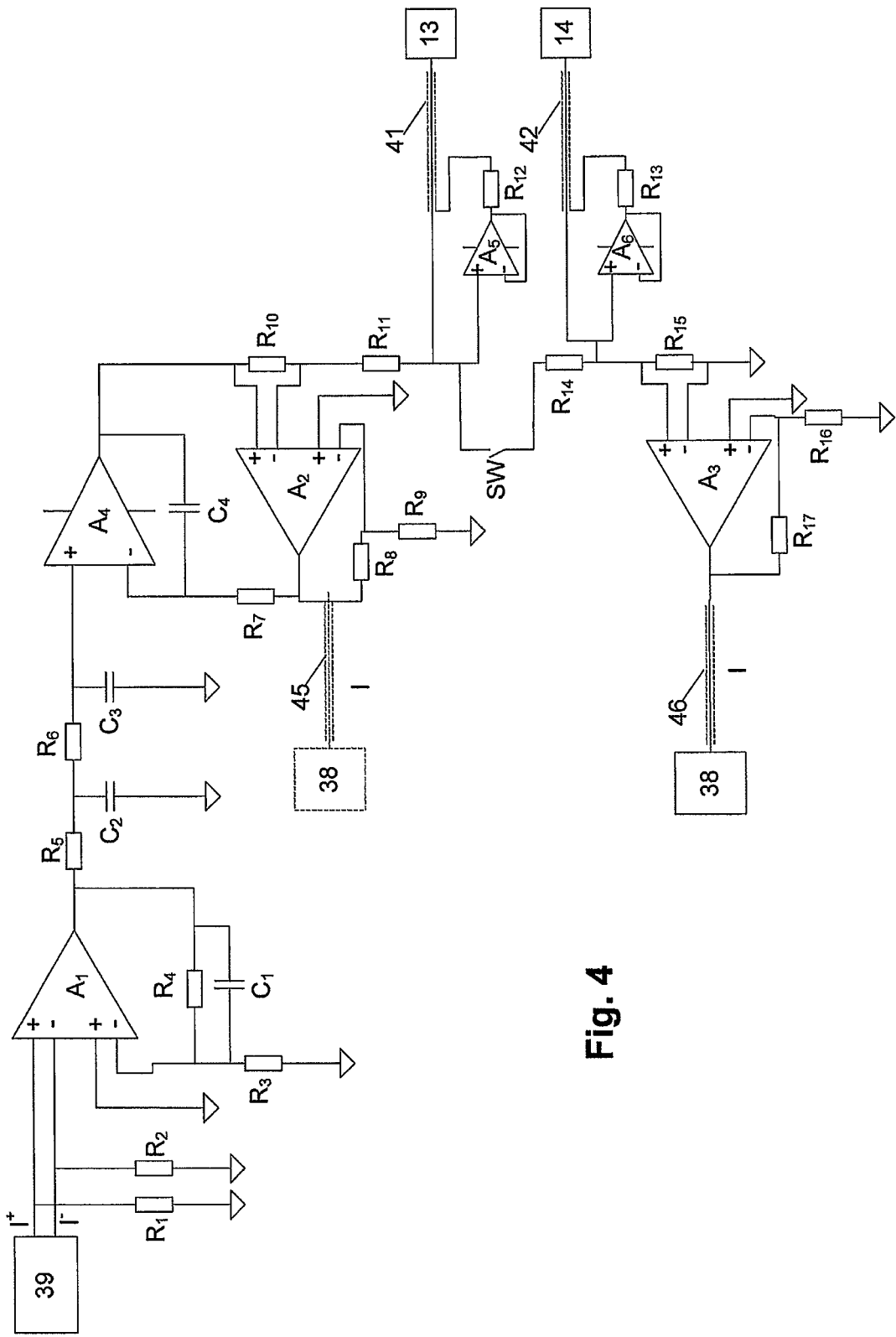
FIG. 4 is a schematic of an example of a current source circuit.

An example of a specific form of signal generator 11 in the form of a current source circuit, is shown in FIG. 4.

As shown the current source includes three fixed or variable gain differential amplifiers $A_1$, $A_2$, $A_3$ and three op-amps $A_4$, $A_5$, $A_6$, a number of resistors $R_1, \ldots R_{17}$ and capacitors $C_1, \ldots C_4$, interconnected as shown. The current source also includes leads 41, 42 (corresponding to the leads L in FIG. 1) which connect the current source to the electrodes 13, 14 and a switch SW for shorting the leads 41, 42 as will be described in more detail below.

Connections 45, 46 can also be provided for allowing the current applied to the subject S to be determined Typically this is achieved using the connection 46. However, the connection 45 may also be used as shown in dotted lines to allow signal losses within the leads and other circuitry to be taken into account.

In general the leads used are co-axial cables with a non-braided shield and a multi strand core with a polystyrene dielectric. This provides good conductive and noise properties as well as being sufficiently flexible to avoid issues with connections from the measuring device 1 to the subject S. In this instance, resistors $R_{12}$, $R_{13}$ decouple the outputs of the amplifiers $A_5$, $A_6$ from the capacitances associated with cable.

In use, the current source circuit receives current control signals $I^+$, $I^-$ from the DAC 39, with these signals being filtered and amplified, to thereby form current signals that can be applied to the subject S via the electrodes 13, 14.

In use, when the amplifiers $A_1$, . . . . $A_6$ are initially activated, this can lead to a minor, and within safety limits, transient current surge. As the current is applied to the subject, this can result in the generation of a residual field across the subject S. To avoid this field effecting the readings, the switch SW is generally activated prior to measurements being taken, to short the current circuit, and thereby discharge any residual field.

Once the measurement is commenced, an indication of the current applied to the subject can be obtained via either one of the connections 45, 46, that are connected to the ADC 38, as shown by the dotted lines.

This allows the current supplied across the subject to be accurately determined. In particular, by using the actual applied current, as opposed to estimating the current applied on the basis of the control signals $I^+$, $I^-$, this takes into account non-ideal behaviour of the components in the current source, and can also take into account the effects of the leads 41, 42, on the applied current.

In one example, the amplifier $A_3$ and associated components may be provided on a housing coupled to the electrodes 12, 13, allowing more accurate sensing of the current applied to the subject. In particular, this avoids measuring of cable effects, such as signal loss in the leads L.

The above is an example of a non-symmetric current source and it will be appreciated that symmetric current sources may alternatively be used.

Figure 5:
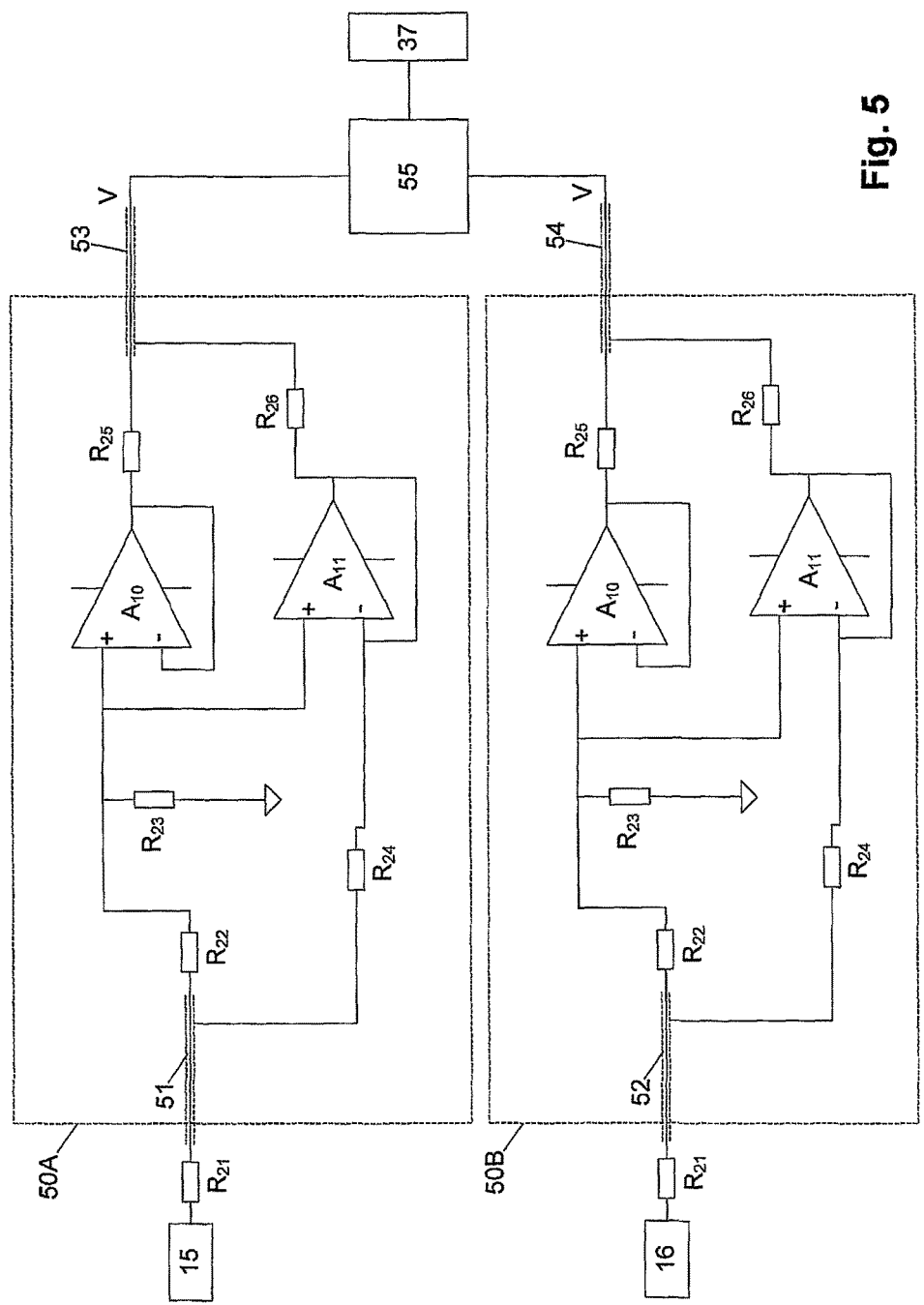
FIG. 5 is a schematic of an example of a buffer circuit for use in voltage sensing.

An example of the buffer used for the voltage electrodes is shown in FIG. 5. In this example, each electrode 15, 16, will be coupled to a buffer circuit 50A, 50B.

In this example, each buffer 50A, 50B includes amplifiers $A_{10}$, $A_{11}$, and a number of resistors $R_{21}$, . . . , $R_{26}$, interconnected as shown. In use, each buffer 50A, 50B, is connected a respective electrode 15, 16 via connections 51, 52. The buffers 50A, 50B are also connected via leads 53, 54 to a differential amplifier 55, acting as the signal sensor 12, which is in turn coupled to the ADC 37. It will therefore be appreciated that a respective buffer circuit 50A, 50B is connected to each of the electrodes 15, 16, and then to a differential amplifier, allowing the potential difference across the subject to be determined.

In one example, the leads 53, 54 correspond to the leads L shown in FIG. 1, allowing the buffer circuits 50A, 50B to be provided in connector housing coupled to the electrodes 15, 16, as will be described in more detail below.

In use, the amplifier $A_{10}$ amplifies the detected signals and drives the core of the cable 53, whilst the amplifier $A_{11}$ amplifies the detected signal and drives the shield of the cables 51, 53. Resistors $R_{26}$ and $R_{25}$ decouple the amplifier outputs from the capacitances associated with cable, although the need for these depends on the amplifier selected.

Again, this allows multi-core shielded cables to be used to establish the connections to the voltage electrodes 15, 16.

Figure 6A:
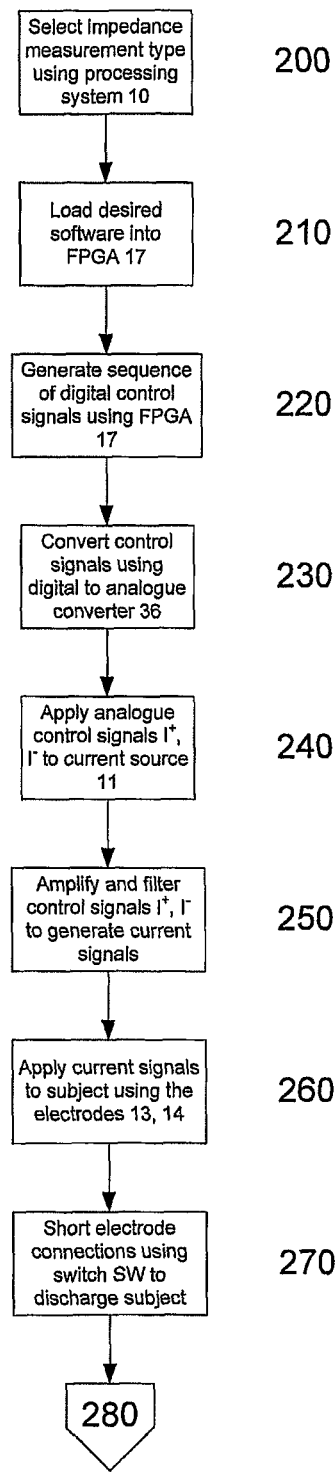
FIGS. 6A and 6B is a flowchart of a second example of a process for performing impedance determination.
Figure 6B:
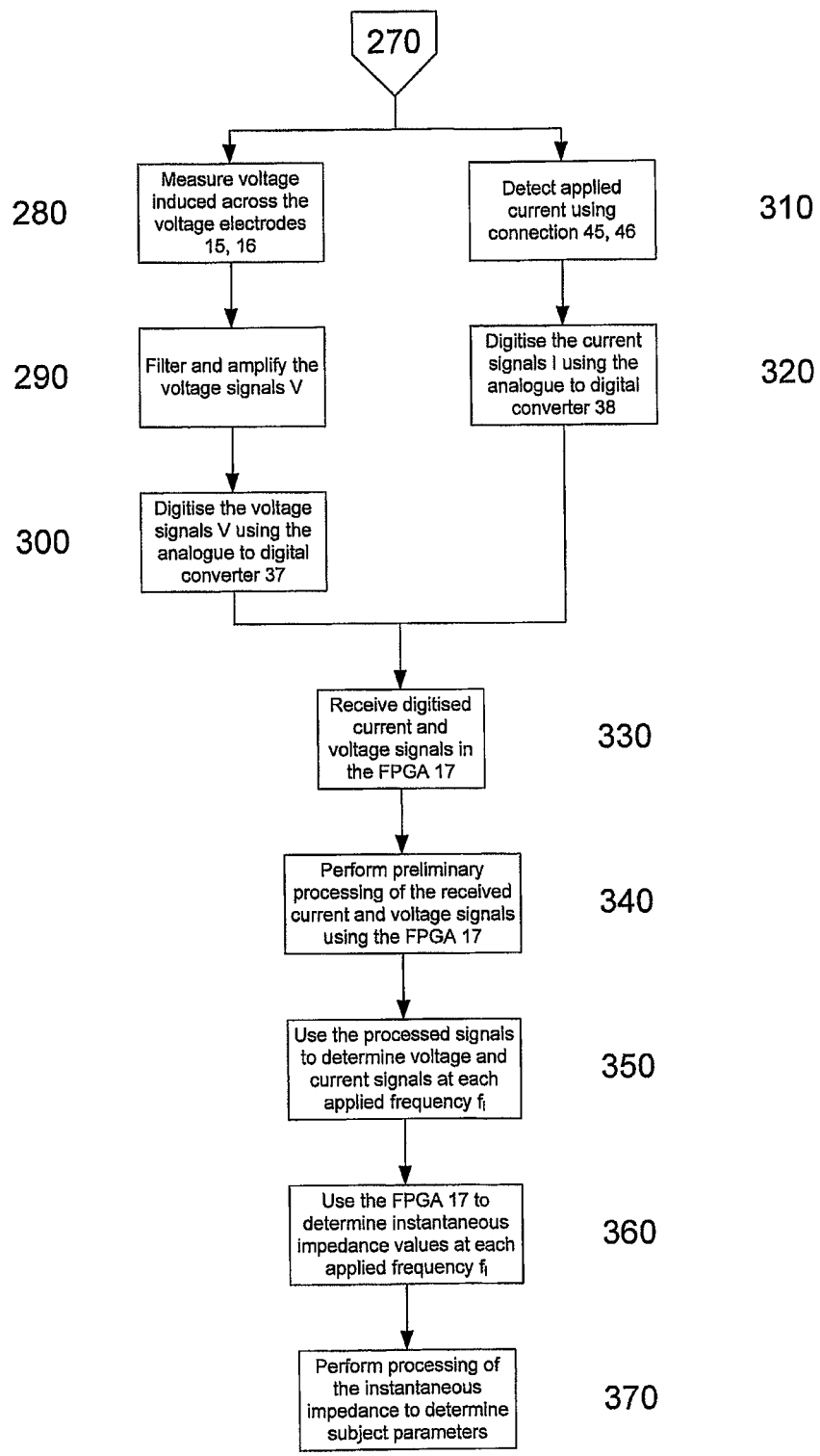

An example of operation of the apparatus will now be described with reference to FIGS. 6A to 6C.

At step 200 an operator selects an impedance measurement type using the first processing system 10. This may be achieved in a number of ways and will typically involve having the first processing system 10 store a number of different profiles, each of which corresponds to a respective impedance measurement protocol.

Thus, for example, when performing cardiac function determination, it will be typical to use a different applied current sequence and a different impedance analysis, as compared to performing lymphoedema measurements, body composition, pulmonary oedema, or the like. The profile will typically be stored in the memory 21, or alternatively may be downloaded from flash memory (not shown), or via the external interface 23.

Once an appropriate measurement type has been selected by the operator, this will cause the first processing system 10 to load desired code module firmware into the programmable module 36 of the second processing system 17 at step 210, or cause embedded firmware to be activated. The type of code module used will depend on the preferred implementation, and in one example this is formed from a wishbone code module, although this is not essential.

At step 220, the second processing system 17 is used to generate a sequence of digital control signals, which are transferred to the DAC 39 at step 230. This is typically achieved using the processing module 34, by having the module generate a predetermined sequence of signals based on the selected impedance measurement profile. This can therefore be achieved by having the second processing system 17 program the processing module 34 to cause the module to generate the required signals.

The DAC 39 converts the digital control signals into analogue control signals $I^+$, $I^-$ which are then applied to the current source 11 at step 240.

As described above, the current source circuit shown in FIG. 4 operates to amplify and filter the electrical control signals $I^+$, $I^-$ at step 250, applying the resulting current signals to the electrodes 13, 14 at step 260.

During this process, and as mentioned above, the current circuit through the subject can optionally be shorted at step 270, using the switch SW, to thereby discharge any residual field in the subject S, prior to readings being made.

At step 280, the measurement procedure commences, with the voltage across the subject being sensed from the electrodes 15, 16. In this regard, the voltage across the electrodes is filtered and amplified using the buffer circuit shown in FIG. 5 at step 290, with the resultant analogue voltage signals V being supplied to the ADC 37 and digitised at step 300. Simultaneously, at step 310 the current applied to the subject S is detected via one of the connections 45, 46, with the analogue current signals I being digitised using the ADC 38 at step 320.

The digitised voltage and current signals V, I are received by the processing modules 32, 33 at step 330, with these being used to performed preliminary processing of the signals at step 340.

The processing performed will again depend on the impedance measurement profile, and the consequent configuration of the processing modules 32, 33. This can include for example, processing the voltage signals V to extract ECG signals. The signals will also typically be filtered to ensure that only signals at the applied frequencies are used in impedance determination. This helps reduce the effects of noise, as well as reducing the amount of processing required.

At step 350 the second processing system 17 uses the processing signals to determine voltage and current signals at each applied frequency $f_i$, with these being used at step 360 to determine instantaneous impedance values at each applied frequency $f_i$.

The ADCs 37, 38 and the processing modules 32, 33 are typically adapted to perform sampling and processing of the voltage and current signals V, I in parallel so that the voltage induced at the corresponding applied current are analysed simultaneously. This reduces processing requirements by avoiding the need to determine which voltage signals were measured at which applied frequency. This is achieved by having the processing modules 32, 33 sample the digitised signals received from the ADCs 37, 38, using a common clock signal generated by the processing module 36, which thereby ensures synchronisation of the signal sampling.

Once the instantaneous impedance values have been derived, these can undergo further processing in either the first processing system 10, or the second processing system 17, at step 370. The processing of the instantaneous impedance signals will be performed in a number of different manners depending on the type of analysis to be used and this in turn will depend on the selection made by the operator at step 200.

Accordingly, it will be appreciated by persons skilled in the art that a range of different current sequences can be applied to the subject by making an appropriate measurement type selection. Once this has been performed, the FPGA operates to generate a sequence of appropriate control signals $I^+$, $I^-$, which are applied to the subject S using the current supply circuit shown in FIG. 4. The voltage induced across the subject is then sensed using the buffer circuit shown in FIG. 5, allowing the impedance values to be determined and analysed by the second processing system 17.

Using the second processing system 17 allows the majority of processing to be performed using custom configured hardware. This has a number of benefits.

Firstly, the use of an second processing system 17 allows the custom hardware configuration to be adapted through the use of appropriate firmware. This in turn allows a single measuring device to be used to perform a range of different types of analysis.

Secondly, this vastly reduces the processing requirements on the first processing system 10. This in turn allows the first processing system 10 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of lymphoedema.

Thirdly, this allows the measuring device 1 to be updated. Thus for example, if an improved analysis algorithms is created, or an improved current sequence determined for a specific impedance measurement type, the measuring device can be updated by downloading new firmware via flash memory (not shown) or the external interface 23.

It will be appreciated that in the above examples, the processing is performed partially by the second processing system 17, and partially by the first processing system 10. However, it is also possible for processing to be performed by a single element, such as an FPGA, or a more generalised processing system.

As the FPGA is a custom processing system, it tends to be more efficient in operation than a more generic processing system. As a result, if an FPGA alone is used, it is generally possible to use a reduced overall amount of processing, allowing for a reduction in power consumption and size. However, the degree of flexibility, and in particular, the range of processing and analysis of the impedance which can be performed is limited.

Conversely, if only a generic processing system is used, the flexibility is enhanced at the expensive of a decrease in efficiency, and a consequent increase in size and power consumption.

Accordingly, the above described example strikes a balance, providing custom processing in the form of an FPGA to perform partial processing. This can allow for example, the impedance values to be determined Subsequent analysis, which generally requires a greater degree of flexibility can then be implemented with the generic processing system.

A further disadvantage of utilising an FPGA alone is that it complicates the process of updating the processing, for example, if improved processing algorithms are implemented.

Electrode Connections

Figure 7A:
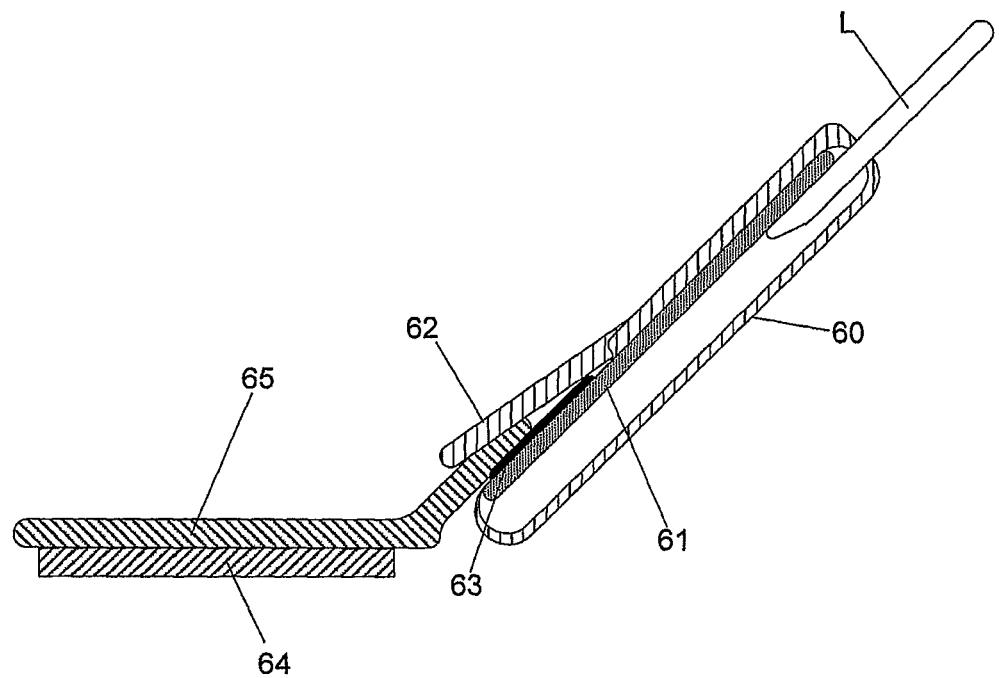
FIGS. 7A and 7B are schematics of an example of an electrode connection.
Figure 7B:
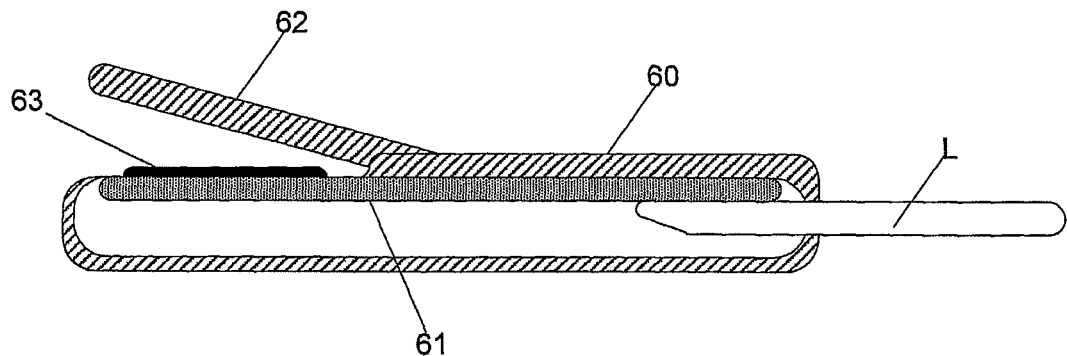

An example of an electrode connection apparatus is shown in FIGS. 7A and 7B.

In particular, in this example, the connector includes circuitry provided on a substrate such as a PCB (Printed Circuit Board) 61, which is in turn mounted in a housing 60 as shown. The housing 60 includes an arm 62 which is urged toward a contact 63 provided on the substrate 61. The substrate 61 is then coupled to a respective one of the ADCs 37, 38 or the DAC 39, via appropriate leads shown generally at L, such as the leads 41, 42, 53, 54.

In use, the connector couples to a conductive electrode substrate 65, such as a plastic coated in silver, and which in turn has a conductive gel 64, such as silver/silver chloride gel thereon. The arm 62 urges the conductive electrode substrate 65 against the contact 63, thereby electrically coupling the conductive gel 64 to the circuit provided on the substrate 61.

This ensures good electrical contact between the measuring device 1 and the subject S, as well as reducing the need for leads between the electrodes 13, 14 and the input of the voltage buffers, removing the requirement for additional leads, which represents an expense, as well as a source of noise within the apparatus.

In this example, the edges and corners of the housing 60, the arm 62 and the substrate 65 are curved. This is to reduce the chance of a subject being injured when the connector is attached to the electrode. This is of particular importance when using the electrodes on lymphodema suffers, when even a small nip of the skin can cause severe complications.

To further enhance the useability of the housing, the housing may be formed from a material that has a low coefficient of friction and/or is spongy or resilient. Again, these properties help reduce the likelihood of the subject being injured when the housing is coupled to the electrode.

Electrical Isolation

Figure 8:
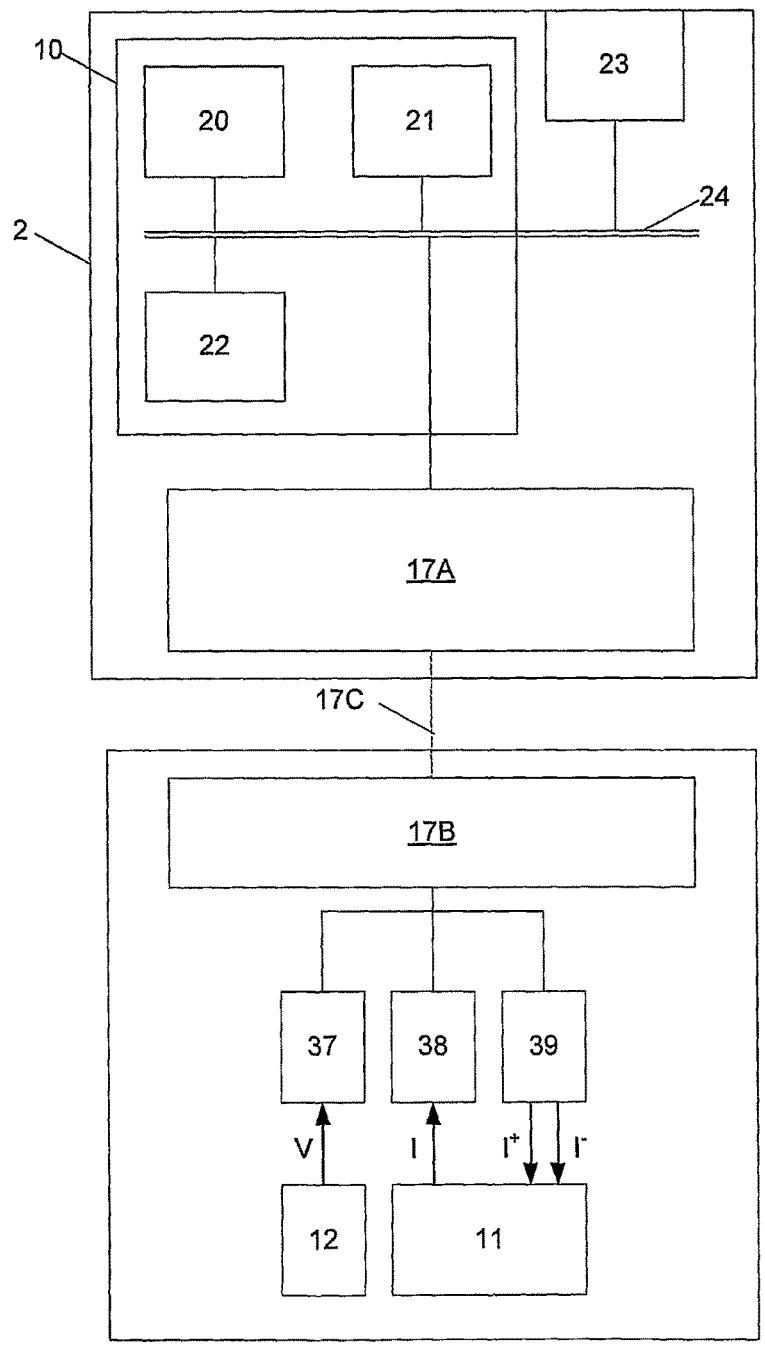
FIG. 8 is a schematic of a third example of impedance determination apparatus.

A further development of the apparatus will now be described with reference to FIG. 8.

In this example, the second processing system 17 is formed from two respective FPGA portions 17A, 17B. The two FPGA portions 17A, 17B are interconnected via an electrically isolated connection shown generally by the dotted line 17C. The electrically isolated connection could be achieved for example using an inductive loop connections, wireless links or the like.

This split in the FPGA can be used to ensure that the measuring device 1 is electrically isolated from the subject S. This is important for example when taking readings with a high degree of accuracy.

In this example, the second processing system 17 will typically be implemented such that the operation of the second FPGA portion 17B is substantially identical for all measurement types. As a result, there is no requirement to upload firmware into the second FPGA portion 17B to allow different types of impedance analysis.

In contrast to this, the first FPGA portion 17A will typically implement firmware depending on the impedance measurement type in a manner substantially as described above.

It will therefore be appreciated that this provides a mechanism by which the measuring device 1 is electrically isolated from the subject, whilst still allowing the benefits of use of the second processing system 17 to be achieved.

Alternatively, equivalent electrical isolation can be obtained by providing a single FPGA electrically isolated from the first processing system 10.

In this example, the second FPGA portion 17B can be provided into a subject unit, shown generally at 2, which includes the lead connections.

This allows a single measuring device 1 to communicate with a number of different subject units, each of which is associated with a respective subject S. This allows the measuring device 1 to provide centralised monitoring of a number of different subjects via way of a number of subject units 2. This in turn allows a number of subjects to be analysed in sequence without having to reconnect each subject S each time an analysis is to be performed.

Lead Calibration

To assist in interpreting the impedance measurements, it is useful to take into account electrical properties of the connecting leads and associated circuitry.

To achieve this, the leads and corresponding connections can be encoded with calibration information. This can include, for example, using specific values for respective ones of the resistors in the current source, or buffer circuits shown in FIGS. 4 and 5. Thus for example, the value of the resistors $R_{12}$, $R_{13}$, $R_{26}$ can be selected based on the properties of the corresponding leads.

In this instance, when the leads are connected to the measuring device 1, via the corresponding ADCs 37, 38, the processing modules 32, 33 can be to interrogate the circuitry using appropriate polling signals to thereby determine the value of corresponding resistor. Once this value has been determined, the second processing system 17 can use this to modify the algorithm used for processing the voltage and current signals to thereby ensure correct impedance values are determined.

In addition to this, the resistance value can also act as a lead identifier, to allow the measuring device to identify the leads and ensure that only genuine authorised leads are utilised. Thus, for example, if the determined resistance value does not correspond to a predetermined value this can be used to indicate that non-genuine leads are being used. In this instance, as the lead quality can have an effect on the accuracy of the resultant impedance analysis, it may desirable to either generate an error message or warning indicating that incorrect leads are in use. Alternatively, the second processing system 17 can be adapted to halt processing of the measured current and voltage signals. This allows the system to ensure that only genuine leads are utilised.

This can further be enhanced by the utilisation of a unique identifier associated with each lead connection circuit. In this instance, a unique identifier can be encoded within an IC provided as part of the current source or voltage buffer circuits. In this instance, the measuring device 1 interrogates the unique identifier and compared to unique identifiers stored either in local memory, or in a central database, allowing genuine leads to be identified.

This process can also be used to monitor the number of times a lead has been used. In this instance, each time a lead is used, data reflecting lead usage is recorded. This allows the leads to have a predesignated use quota life span, and once the number of times the lead is used reaches the quota, further measurements using the leads can be prevented. Similarly, a temporal limitation can be applied by providing an expiry date associated with the lead. This can be based on the date the lead is created, or first used depending on the preferred implementation.

It will be appreciated that when recording lead usage, issues may arise if this is recorded locally. In particular, this could allow a lead to be re-used with a different measuring device. To avoid this, the leads can be configured with a ID which is set by the measuring device on first use. This can be used to limit usage of the leads to a single measuring device.

This can be used to ensure that the leads are correctly replaced in accordance with a predetermined lifespan thereby helping to ensure accuracy of measure impedance values.

Multiple Channel

Figure 9:
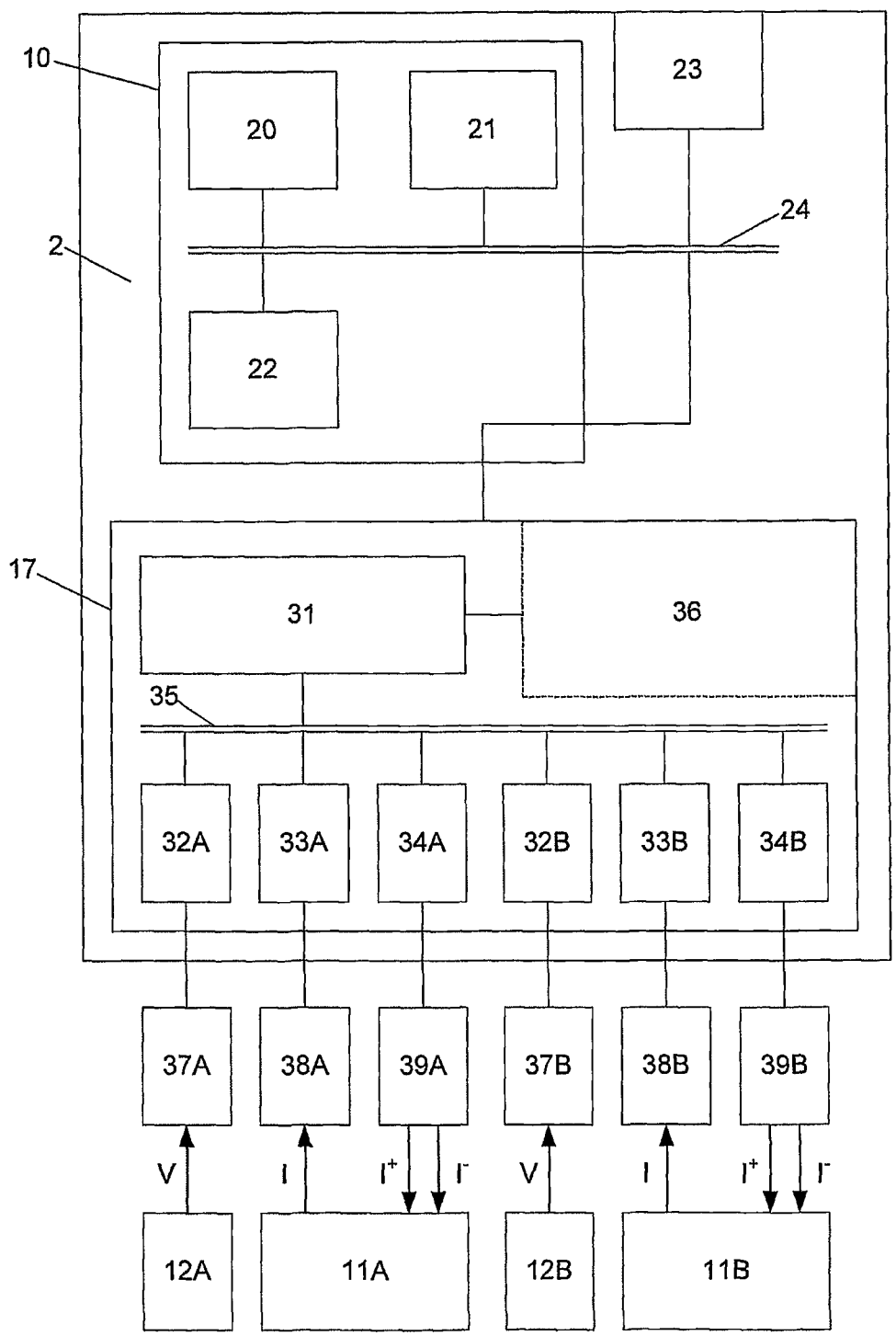
FIG. 9 is a schematic of a fourth example of impedance determination apparatus; and, FIG. 10 is a schematic of a fifth example of impedance determination apparatus.

A further variation to the apparatus is shown in FIG. 9.

In this example, the apparatus is adapted to provide multiple channel functionality allowing different body segments to undergo impedance analysis substantially simultaneously. In this instance, this is achieved by providing first and second processing modules 32A, 32B, 33A, 33B, 34A, 34B, first and second ADCs and DACs 37A, 37B, 38A, 38B, 39A, 39B as well as first and second voltage and current circuits 11A, 11B, 12A, 12B, in parallel, as shown.

Thus, the measuring device 1 includes two separate impedance measuring channels indicated by the use of reference numerals A, B. In this instance, this allows electrodes to be attached to body segments, such as different limbs, with measurements being taken from each segment substantially simultaneously.

As an alternative to the above described arrangement, multiple channels could alternatively be implemented by utilising two separate second processing modules 17, each one being associated with a respective channel. Alternatively, the signals applied to each channel could be applied via multiplexers positioned between the ADCs 37, 38 and the DAC 39 and the electrodes.

It will be appreciated that whilst two channels are shown in the above example, this is for clarity only, and any number of channels may be provided.

Switching Arrangement

Figure 10:
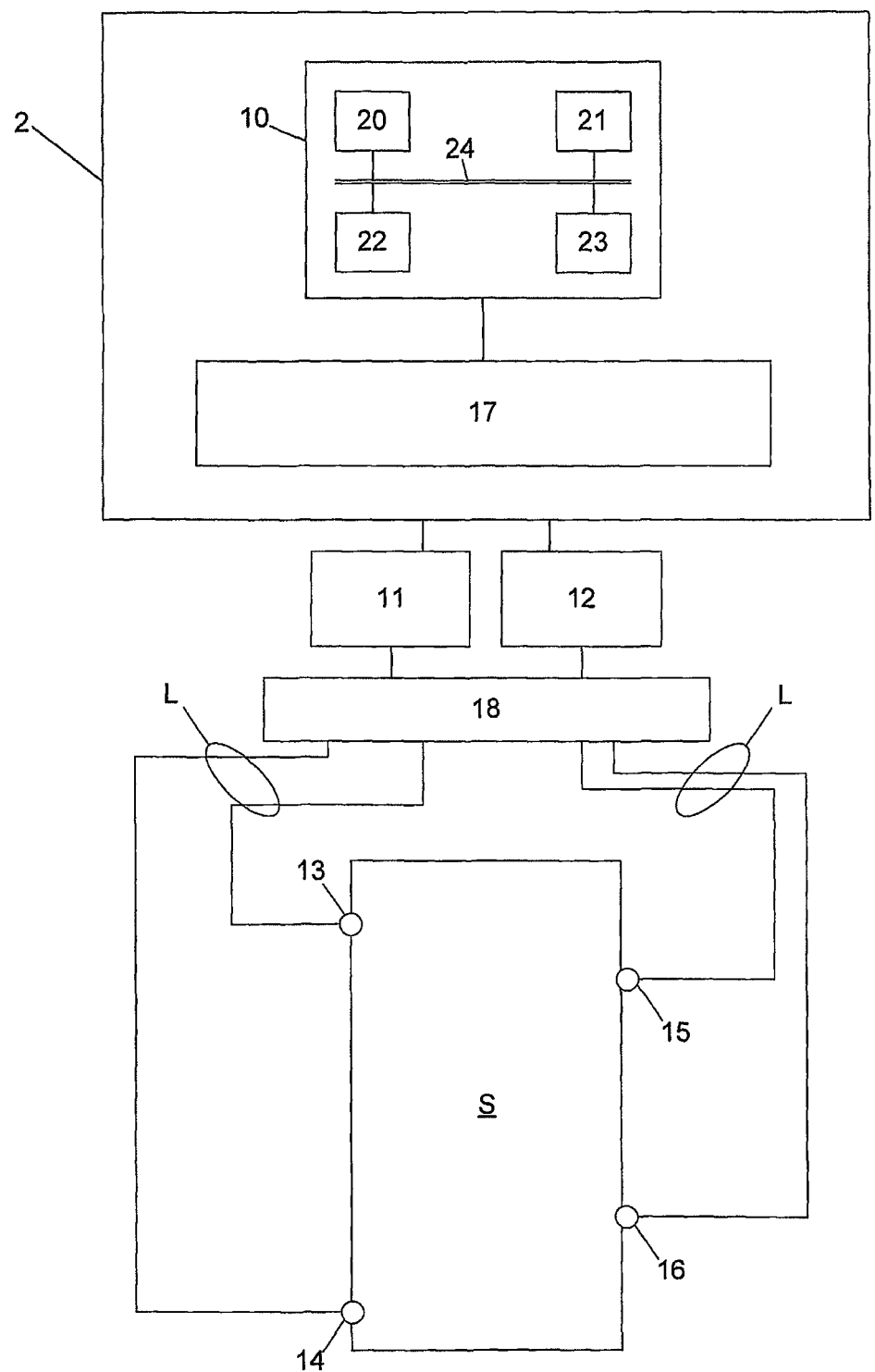

FIG. 10 shows an example of an impedance measuring apparatus including a switching arrangement. In this example, the measuring device 1 includes a switching device 18, such as a multiplexer, for connecting the signal generator 11 and the sensor 12 to the leads L. This allows the measuring device 1 to control which of the leads L are connected to the signal generator 11 and the sensor 12.

In this example, a single set of leads and connections is shown. This arrangement can be used in a number of ways. For example, by identifying the electrodes 13, 14, 15, 16 to which the measuring device 1 is connected, this can be used to control to which of the leads L signals are applied, and via which leads signals can be measured. This can be achieved either by having the user provide an appropriate indication via the input device 22, or by having the measuring device 1 automatically detect electrode identifiers, as will be described in more detail below.

Alternatively, however the arrangement may be used with multiple leads and electrodes to provide multi-channel functionality as described above.

Electrode Configuration

Figure 11A:
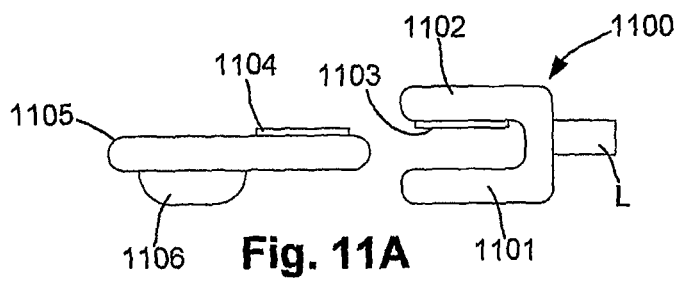
FIGS. 11A and 11B are schematic diagrams of a second example of an electrode connection.
Figure 11B:
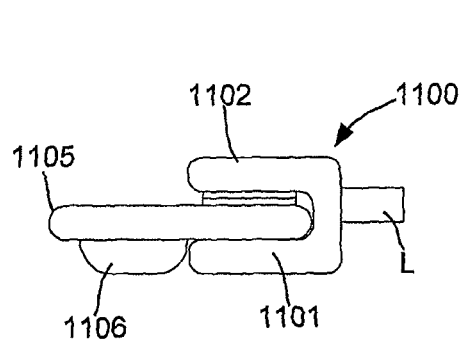
Figure 11C:
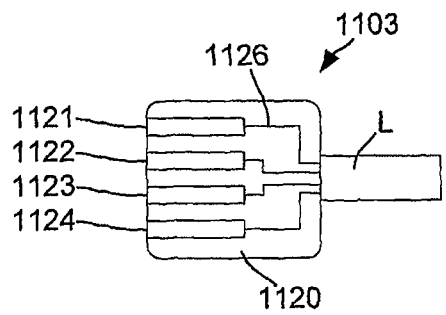
FIGS. 11C to 11G are schematic diagrams of a third example of an electrode connection.
Figure 11D:
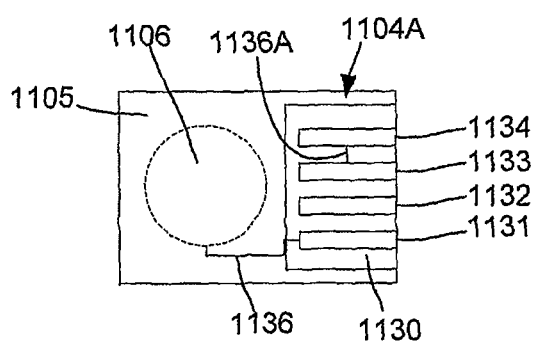
Figure 11E:
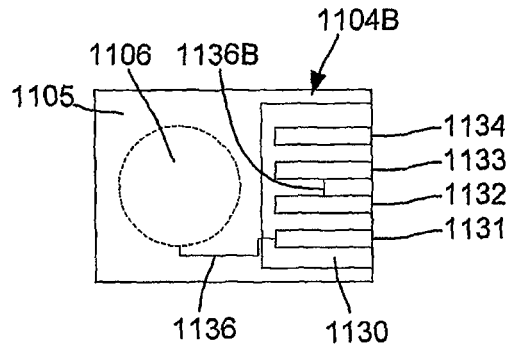
Figure 11F:
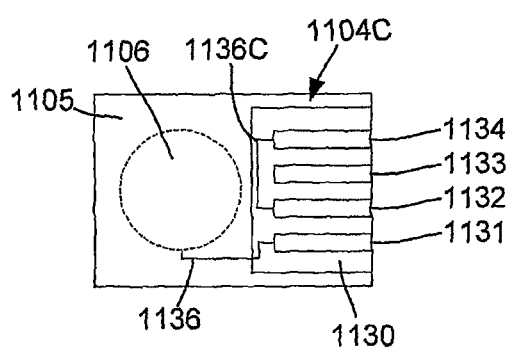
Figure 11G:
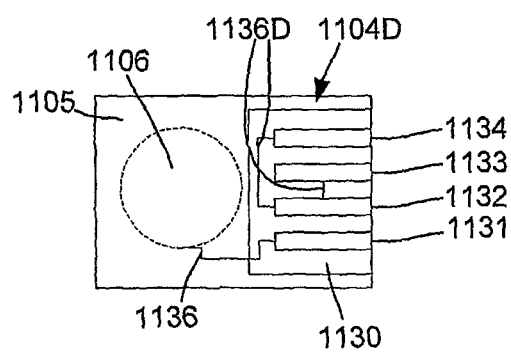

An example of an alternative electrode configuration will now be described with reference to FIGS. 11A and 11B.

In this example, the electrode connector is formed from a housing 1100 having two arms 1101, 1102 arranged to engage with an electrode substrate 1105 to thereby couple the housing 1100 to the substrate 1105. A contact 1103 mounted on an underside of the arm 1102, is urged into contact and/or engagement with an electrode contact 1104 mounted on a surface of the electrode substrate 1105. The electrode also includes a conductive gel 1106, such as a silver/silver chloride gel, electrically connected to the contact 1104. This can be achieved, either by using a conductive track, such as a silver track, or by using a conductive substrate such as plastic coated in silver.

This allows the lead L to be electrically connected to the conductive gel 1106, allowing current to be applied to and/or a voltage measured from the subject S to which they are attached. It will be appreciated that in this example the above described housing 1100 may also contain the buffer circuit 50, or all or part of the current source circuit shown in FIG. 4, in a manner similar to that described above with respect to FIG. 7.

Alternatively more complex interconnections may be provided to allow the measuring device 1 to identify specific electrodes, or electrode types.

This can be used by the measuring device 1 to control the measurement procedure. For example, detection of an electrode type by the processing system 2 may be used to control the measurements and calculation of different impedance parameters, for example to determine indicators for use in detecting oedema, monitoring cardiac function, or the like.

Similarly, electrodes can be provided with visual markings indicative of the position on the subject to which the electrode should be attached. For example a picture of a left hand can be shown if the electrode pad is to be attached to a subject's left hand. In this instance, identification of the electrodes can be used to allow the measuring device 1 to determine where on the subject the electrode is attached and hence control the application and measurement of signals accordingly.

An example of this will now be described with reference to FIGS. 11C to 11G. In this example the contact 1103 is formed from a contact substrate 1120, such as a PCB, having a number of connector elements 1121, 1122, 1123, 1124, formed from conductive contact pads, typically made of silver or the like. The connector elements are connected to the lead L via respective electrically conductive tracks 1126, typically formed from silver, and provided on the contact substrate 1120. The lead L includes a number of individual wires, each electrically coupled to a respective one of the connector elements 1121, 1122, 1123, 1124.

In this example the electrode contact 1104 on the electrode substrate 1105 typically includes an electrode contact substrate 1130, including electrode connector elements 1131, 1132, 1133, 1134, typically formed from silver contact pads or the like. The electrode connector elements 1131, . . . 1134 are positioned so that, in use, when the electrode connector 1100 is attached to an electrode, the connector elements 1121 . . . 1124 contact the electrode connector elements 1131, . . . 1134 to allow transfer of electrical signals with the measuring device 1.

In the examples, of FIGS. 11D to 11G, the connector element 1131 is connected to the conductive gel 1106, via an electrically conductive track 1136, typically a silver track that extends to the underside of the electrode substrate 1105. This can be used by the measuring device 1 to apply a current to, or measure a voltage across the subject S.

Additionally, selective ones of the connector elements 1132, 1133, 1134 are also interconnected in four different arrangements by respective connectors 1136A, 1136B, 1136C, 1136D. This allows the measuring device 1 to detect which of the electrode contacts 1122, 1123, 1124 are interconnected, by virtue of the connectors, 1136A, 1136B, 1136C, 1136D, with the four different combinations allowing the four different electrodes to be identified.

Accordingly, the arrangement of FIGS. 11D to 11G can be used to provide four different electrodes, used as for example, two current supply 13, 14 and two voltage measuring electrodes 15, 16.

In use, the measuring device 1 operates by having the second processing system 17 cause signals to be applied to appropriate wires within each of the leads L, allowing the conductivity between the connecting elements 1122, 1123, 1124, to be measured. This information is then used by the second processing system 17 to determine which leads L are connected to which of the electrodes 13, 14, 15, 16. This allows the first processing system 10 or the second processing system 17 to control the multiplexer 18 in the example of FIG. 10, to correctly connect the electrodes 13, 14, 15, 16 to the signal generator 11, or the signal sensor 12.

In this example, the individual applying the electrode pads to the subject can simply position the electrodes 13, 14, 15, 16 on the subject in the position indicated by visual markings provided thereon. Leads may then be connected to each of the electrodes allowing the measuring device 1 to automatically determine to which electrode 13, 14, 15, 16 each lead L connected and then apply current signals and measure voltage signals appropriately. This avoids the complexity of ensuring the correct electrode pads are connected via the correct leads L.

It will be appreciated that the above described process allows electrode identification simply by applying currents to the electrode connector. However, other suitable identification techniques can be used, such as through the use of optical encoding. This could be achieved for example, by providing a visual marker, or a number of suitably arranged physical markers on the electrode connector 1104, or electrode substrate 1105. These could then be detected using an optical sensor mounted on the connector 1100, as will be appreciated by persons skilled in the art.

Alternatively, the identifier for the electrodes may be identified by an encoded value, represented by, for example, the value of a component in the electrode, such as a resistor or capacitor. It will therefore be appreciated that this can be achieved in a manner similar to that described above with respect to lead calibration.

An example of an alternative electrode configuration will now be described with reference to FIGS. 12A to 12F. In this particular example the electrode is a band electrode 1200, which includes a number of separate electrodes. In this example the electrode is formed from an elongate substrate 1210 such as a plastic polymer coated with shielding material and an overlaying insulating material.

A number of electrically conductive tracks 1220 are provided on the substrate extending from an end of the substrate 1211 to respective conductive contact pads 1230, spaced apart along the length of the substrate in sequence. This allows a connector similar to the connectors described above, but with corresponding connections, to be electrically coupled to the tracks 1220.

The tracks 1220 and the contact pads 1230 may be provided on the substrate 1210 in any one of a number of manners, including for example, screen printing, inkjet printing, vapour deposition, or the like, and are typically formed from silver or another similar material. It will be appreciated however that the tracks and contact pads should be formed from similar materials to prevent signal drift.

Following the application of the contact pads 1230 and the tracks 1220, an insulating layer 1240 is provided having a number of apertures 1250 aligned with the electrode contact pads 1230. The insulating layer is typically formed from a plastic polymer coated with shielding material and an overlaying insulating material.

To ensure adequate conduction between the contact pads 1230, and the subject S, it is typical to apply a conductive gel 1260 to the contact pads 1230. It will be appreciated that in this instance gel can be provided into each of the apertures 1250 as shown.

A removable covering 1270 is then applied to the electrode, to maintain the electrode's sterility and/or moisture level in the gel. This may be in the form of a peel off strip or the like which when removed exposes the conductive gel 1260, allowing the electrode to be attached to the subject S.

In order to ensure signal quality, it is typical for each of the tracks 1220 to comprise a shield track 1221, and a signal track 1222, as shown. This allows the shield on the leads L, such as the leads 41, 42, 51 to be connected to the shield track 1221, with the lead core being coupled to the signal track 1222. This allows shielding to be provided on the electrode, to help reduce interference between applied and measured signals.

This provides a fast straight-forward and cheap method of producing band electrodes. It will be appreciated that similar screen printing techniques may be utilised in the electrode arrangements shown in FIGS. 7A and 7B, and 11A-11G.

The band electrode may be utilised together with a magnetic connector as will now be described with respect to FIGS. 12G and 12H. In this example, the band electrode 1200 includes two magnets 1201A, 1201B positioned at the end 1211 of the substrate 1210. The connector, is formed from a connector substrate 1280 having magnets 1281A, 1281B provided therein. Connecting elements 1282 are also provided, and these would in turn be connected to appropriate leads L.

The magnets 1201A, 1281A; 1201B (not shown for clarity), 1281B can be arranged to align and magnetically couple, to urge the connector substrate 1280 and the band electrode 1200 together.

Correct alignment of the poles of the magnets 1201A, 1281A; 1201B, 1281B can also be used to ensure both the correct positioning and orientation of the connector substrate 1280 and band electrode, which can ensure correct alignment of the connecting elements 1282, with corresponding ones of the tracks 1220, on the band electrode 1200.

It will be appreciated that this can be used to ensure correct connection with the electrode, and that a similar magnetic alignment technique may be used in the connectors previously described.

Figure 12A:
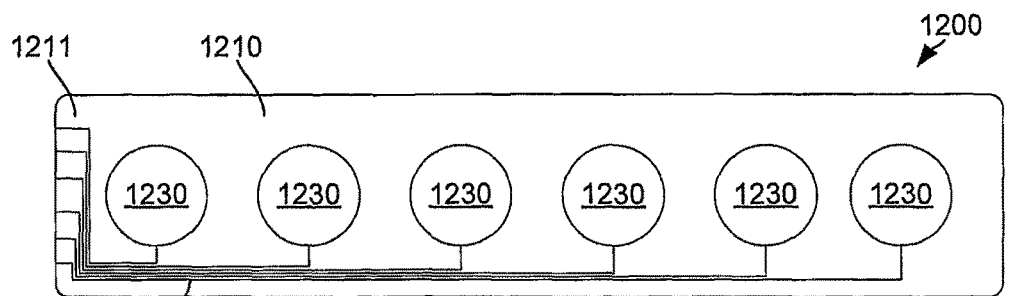
FIGS. 12A to 12F are schematic diagrams of an example of the construction of a band electrode.
Figure 12B:
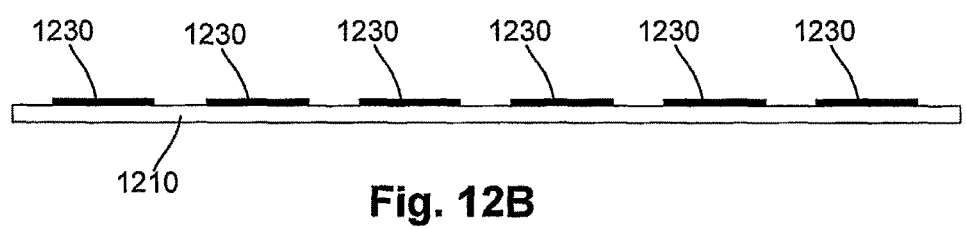
Figure 12C:
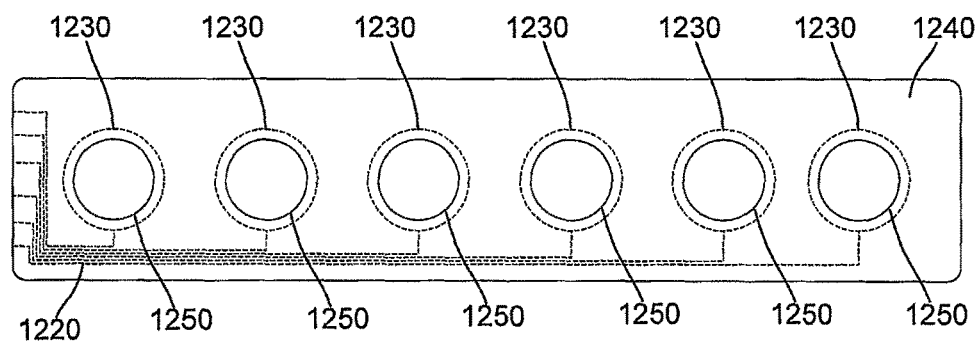
Figure 12D:
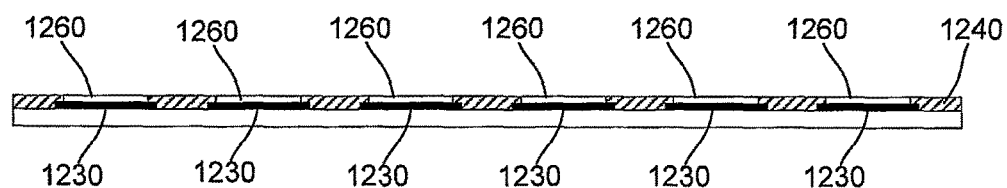
Figure 12E:
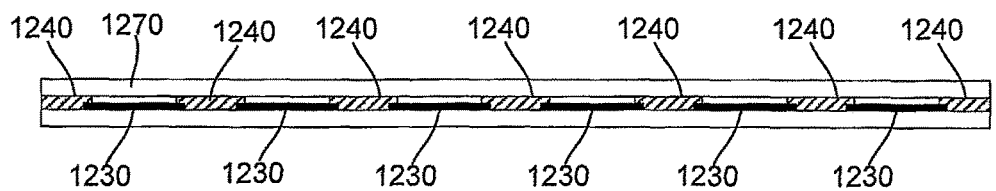
Figure 12F:
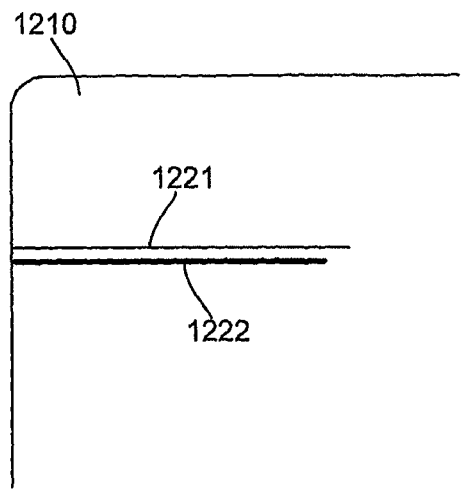
Figure 12I:
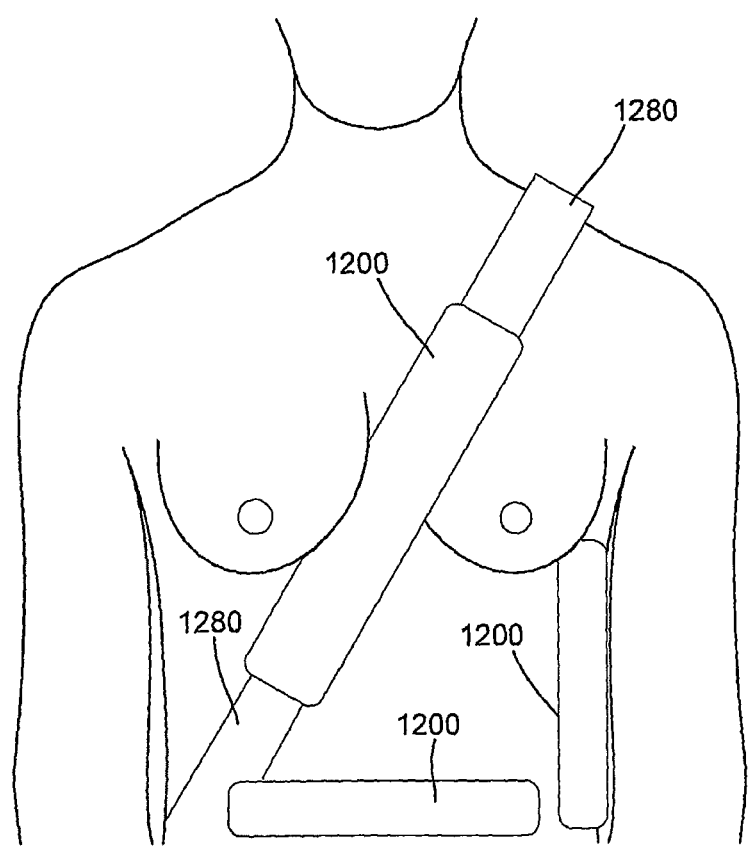
FIG. 12I is a schematic diagram of the use of a band electrode.
Figure 12G:
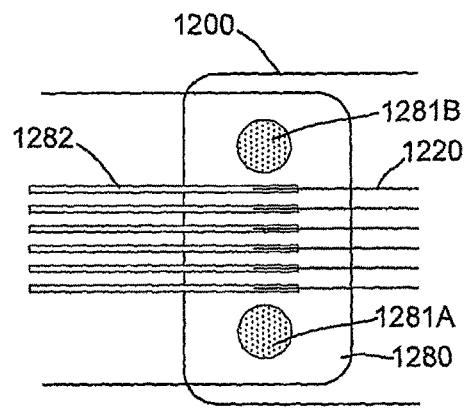
FIGS. 12G and 12H are schematic diagrams of an example of a connector arrangement for the band electrode.
Figure 12H:
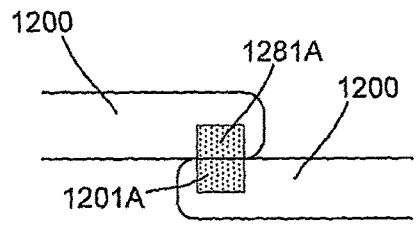

In use, the band electrode may be attached to the subject's torso, as shown in FIG. 12I. The electrode will typically include an adhesive surface, allowing it to stick to the subject. However, a strap 1280 may also be used, to help retain the electrode 1200 in position. This provides an electrode that is easy to attach and position on the subject, and yet can be worn for an extended period if necessary. The band electrode 1200 may also be positioned on the subject at other locations, such as on the side of the subject's torso, or laterally above the naval, as shown.

The band electrode 1200 provides sufficient electrodes to allow cardiac function to be monitored. In the above example, the band electrode includes six electrodes, however any suitable number may be used, although typically at least four electrodes are required.

Variable Current

A further feature that can be implemented in the above measuring device is the provision of a signal generator 11 capable of generating a variable strength signal, such as a variable current. This may be used to allow the measuring device 1 to be utilised with different animals, detect problems with electrical connections, or to overcome noise problems.

Figure 13:
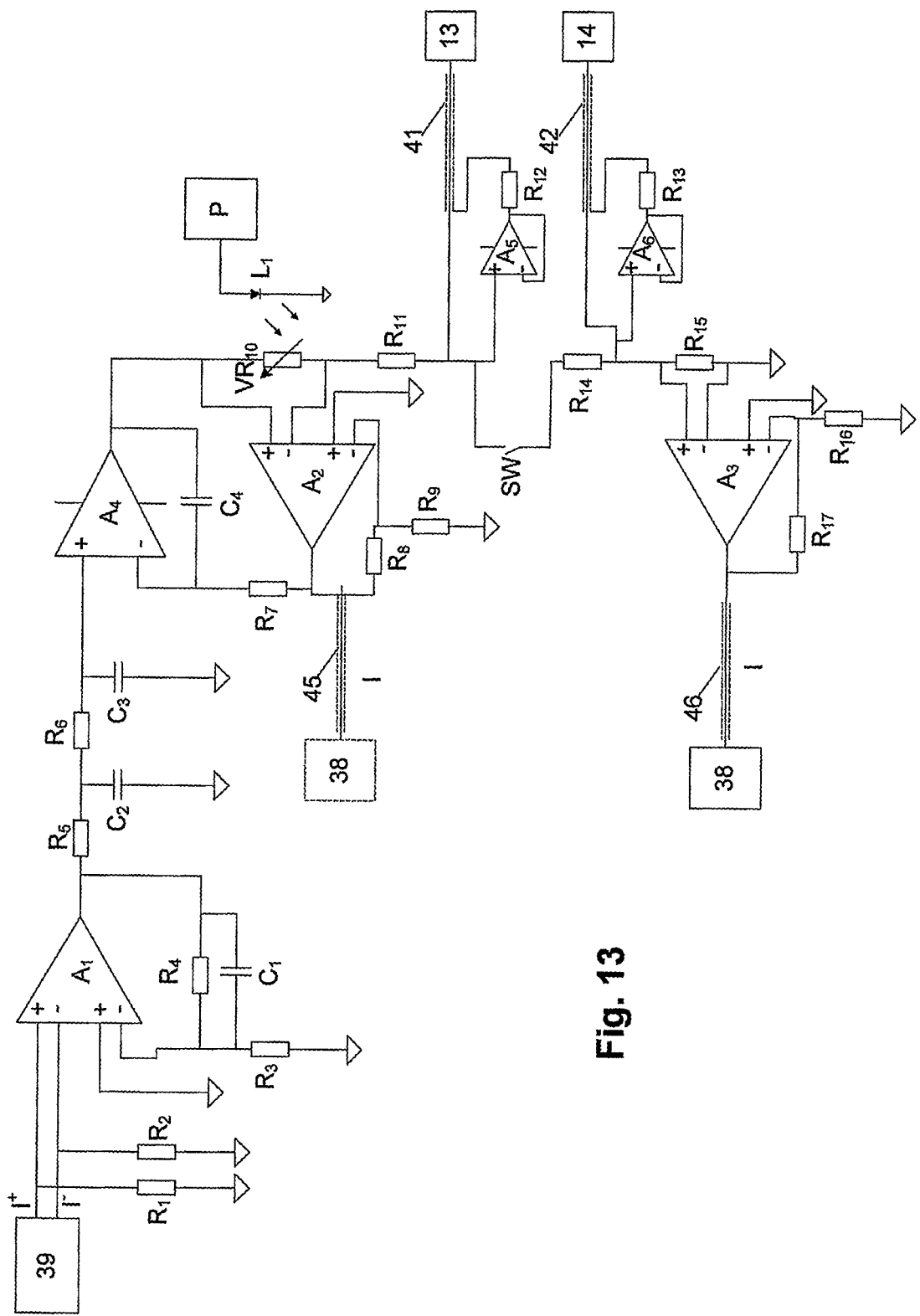
FIG. 13 is a schematic of a second example of a current source circuit.

In order to achieve this, the current source circuit shown in FIG. 4 is modified as shown in FIG. 13. In this example, the resistor $R_{10}$ in the current source circuit of FIG. 4 is replaced with a variable resistor $VR_{10}$. Alteration of the resistance of the resistor $VR_{10}$ will result in a corresponding change in the magnitude of the current applied to the subject S.

To reduce noise and interference between the current source circuit and the control, which is typically achieved using the second processing module 17, it is typical to electrically isolate the variable resistor 17 from the control system. Accordingly in one example, the variable resistor $VR_{10}$ is formed from a light dependent resistor. In this example, an light emitting diode (LED) or other illumination source can be provided, as shown at $L_1$. The LED $L_1$ can be coupled to a variable power supply P of any suitable form. In use, the power supply P, is controlled by the second processing module 17, thereby controlling the intensity of light generated by the LED $L_1$, which in turn allows the resistance $VR_{10}$, and hence the applied current, to be varied.

Figure 14:
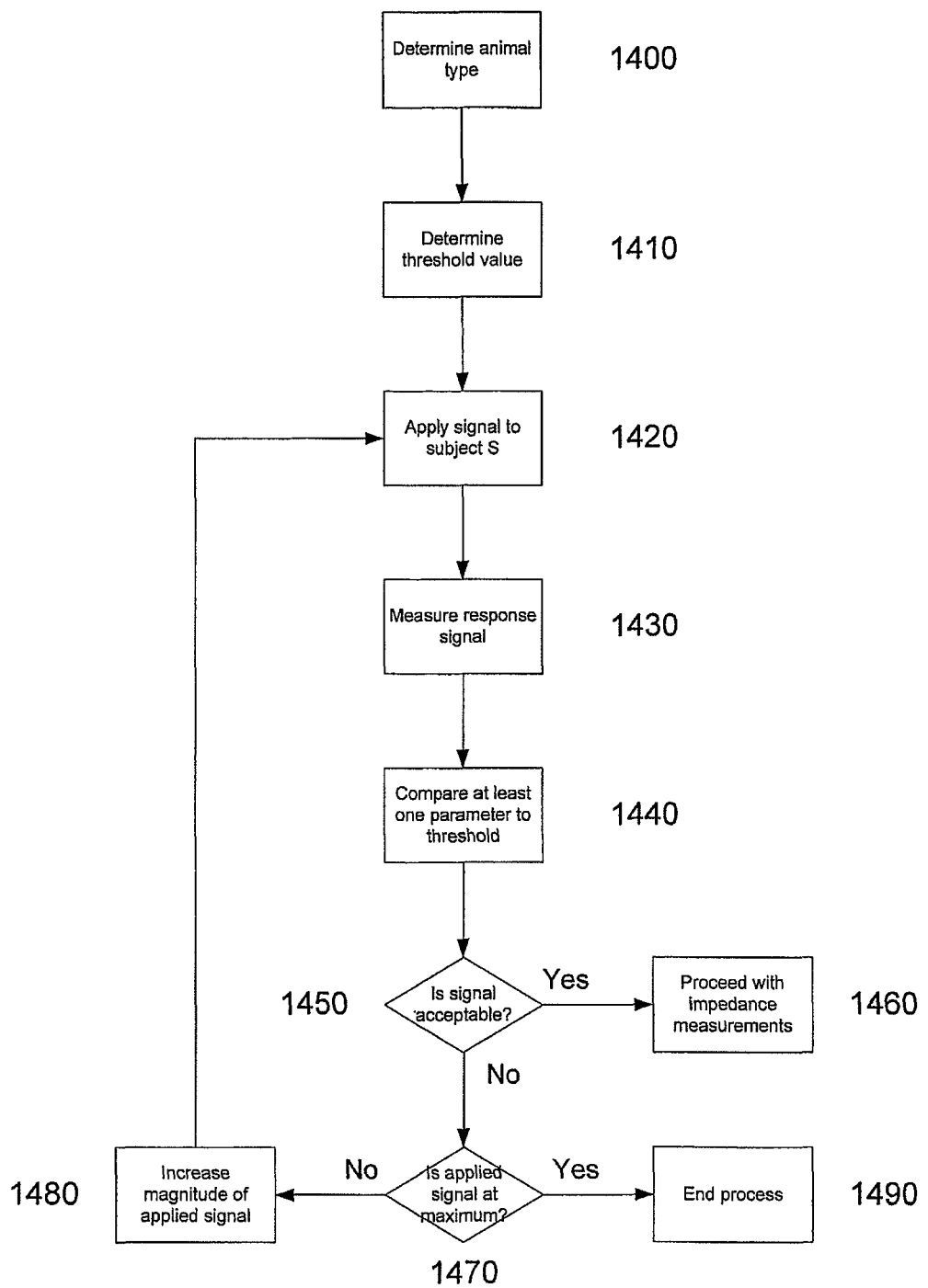
FIG. 14 is a flow chart of an example of using the current source circuit of FIG. 13.

In order to operate the measuring device 1, the first processing system 10 and the second processing system 17 typically implement the process described in FIG. 14. In this example, at step 1400 the user selects a measurement or an animal type utilising the input/output device 22.

At step 1410 the first processing system 10 and the second processing system 17 interact to determine one or more threshold values based on the selected measurement or animal type. This may be achieved in any one of a number of ways, such as by having the first processing system 10 retrieve threshold values from the memory 21 and transfer these to the second processing system 17, although any suitable mechanism may be used. In general, multiple thresholds may be used to specify different operating characteristics, for signal parameters such as a maximum current that can be applied to the subject S, the minimum voltage required to determine an impedance measurement, a minimum signal to noise ratio, or the like.

At step 1420 the second processing system 17 will activate the signal generator 11 causing a signal to be applied to the subject S. At step 1430 the response signal at the electrodes 15,16 is measured using the sensor 12 with signals indicative of the signal being returned to the second processing system 17 at step 1430.

At step 1440 the second processing system 17 compares the at least one parameter of the measured signal to a threshold to determine if the measured signal is acceptable at step 1450. This may involve for example determining if the signal to noise levels within the measured voltage signal are above the minimum threshold, or involve to determine if the signal strength is above a minimum value.

If the signal is acceptable, impedance measurements can be performed at step 1460. If not, at step 1470 the second processing system 17 determines whether the applied signal has reached a maximum allowable. If this has occurred, the process ends at step 1490. However, if the maximum signal has not yet been reached, the second processing system 17 will operate to increase the magnitude of the current applied to the subject S at step 1480 before returning to step 1430 to determine a new measured signal.

Accordingly, this allows the current or voltage applied to the subject S to be gradually increased until a suitable signal can be measured to allow impedance values to be determined, or until either a maximum current or voltage value for the subject is reached.

It will be appreciated that the thresholds selected, and the initial current applied to the subject S in step 1420 will typically be selected depending on the nature of the subject. Thus, for example, if the subject is a human it is typical to utilise a lower magnitude current than if the subject is a animal such as a mouse or the like.

Device Updates

Figure 15:
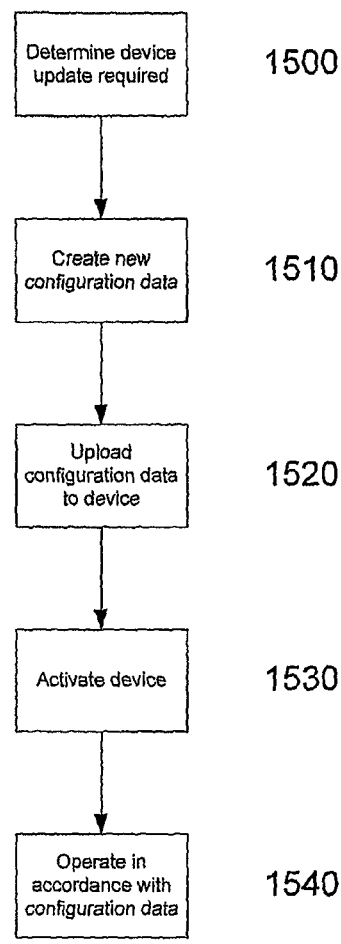
FIG. 15 is a flow chart of an overview of an example of the process of updating a measuring device.

An example of a process for updating the measuring device will now be described with reference to FIG. 15.

In one example, at step 1500 the process involves determining a measuring device 1 is to be configured with an upgrade, or the like, before configuration data is created at step 1510. At step 1520 the configuration data is typically uploaded to the device before the device is activated at 1530. At 1540 when the device commences operation the processing system 2 uses the configuration data to selectively activate features, either for example by controlling the upload of instructions, or by selectively activating instructions embedded within the processing system 2 or the controller 19.

This can be achieved in one of two ways. For example, the configuration data could consist of instructions, such as a software or firmware, which when implemented by the processing system 2 causes the feature to be implemented. Thus, for example, this process may be utilised to update the operation of the firmware provided in the second processing system 17, the processing system 10 or the controller 19 to allow additional functionality, improved measuring algorithms, or the like, to be implemented.

Alternatively, the configuration data could be in the form of a list of features, with this being used by the processing system 2 to access instructions already stored on the measuring device 1. Utilisation of configuration data in this manner, allows the measuring device to be loaded with a number of as yet additional features, but non-operational features, when the device is sold. In this example, by updating the configuration data provided on the measuring device 1, this allows these further features to be implemented without requiring return of the measuring device 1 for modification.

This is particularly useful in the medical industry as it allows additional features to be implemented when the feature receives approval for use. Thus, for example, techniques may be available for measuring or detecting lymphoedema in a predetermined way, such as through the use of a particular analysis of measured voltage signals or the like. In this instance when a device is sold, approval may not yet have been obtained from an administering body such as the Therapeutic Goods Administration, or the like. Accordingly, the feature is disabled by appropriate use of a configuration data. When the measurement technique subsequently gains approval, the configuration data can be modified by uploading a new updated configuration data to the measuring device, allowing the feature to be implemented.

It will be appreciated that these techniques may be used to implement any one of a number of different features, such as different measuring techniques, analysis algorithms, reports on results of measured impedance parameters, or the like.

Figure 16:
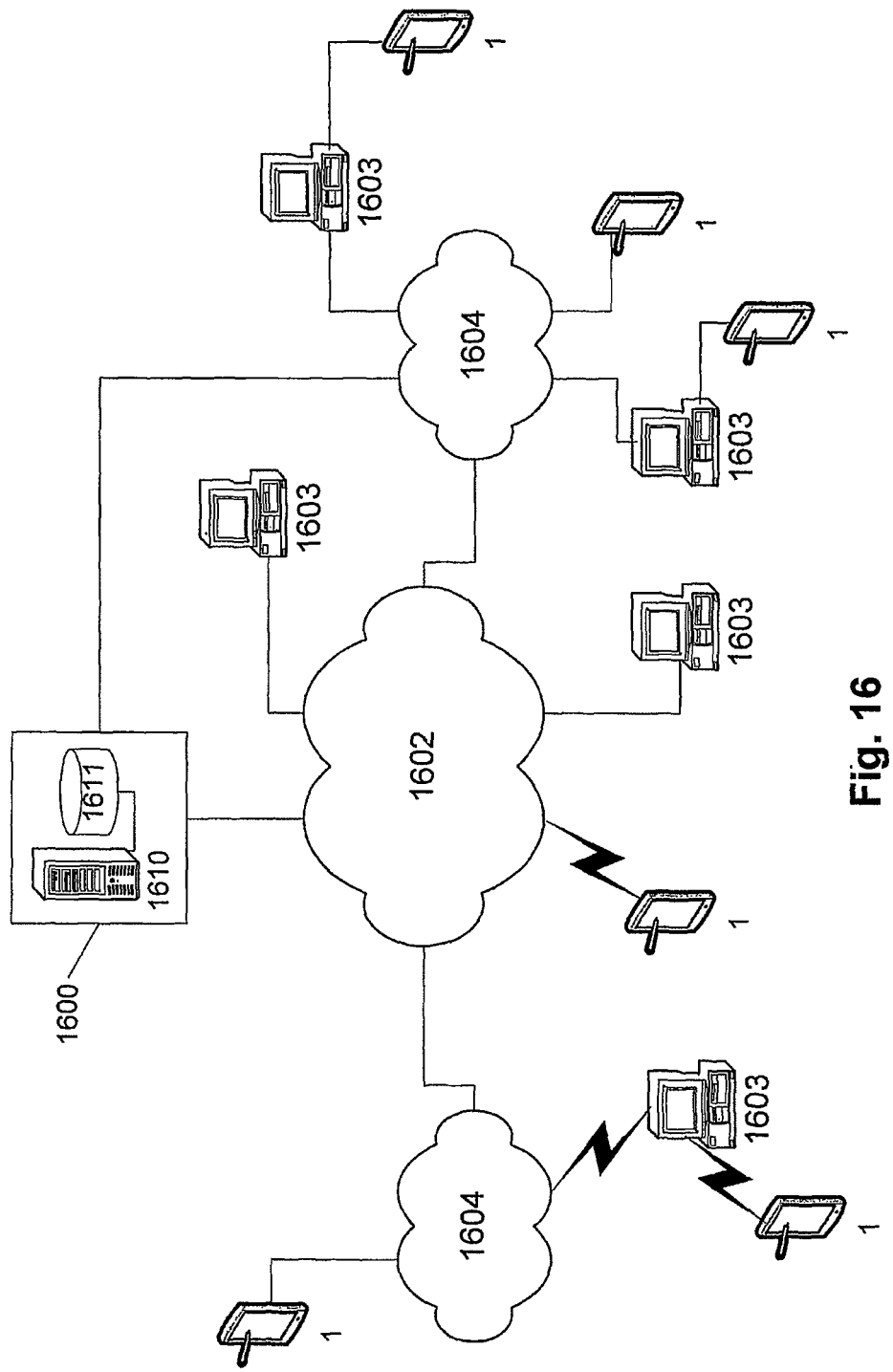
FIG. 16 is a schematic diagram of an example of a system architecture for updating a measuring device.

An example of a suitable system for providing updates will now be described with respect to FIG. 16. In this example, a base station 1600 is coupled to a number of measuring devices 1, and a number of end stations 1603 via a communications network 1602, such as the Internet, and/or via communications networks 1604, such as local area networks (LANs), or wide area networks (WANs). The end stations are in turn coupled to measuring devices 1, as shown.

In use, the base station 1600 includes a processing system 1610, coupled to a database 1611. The base station 1600 operates to determine when updates are required, select the devices to which updates are applied, generate the configuration data and provide this for update to the devices 1. It will be appreciated that the processing system 1610 may therefore be a server or the like.

This allows the configuration data to be uploaded from the server either to a user's end station 1603, such as a desk top computer, lap top, Internet terminal or the like, or alternatively allows transfer from the server via the communications network 1602, 1604, such as the Internet. It will be appreciated that any suitable communications system can be used such as wireless links, wi-fi connections, or the like.

Figure 17:
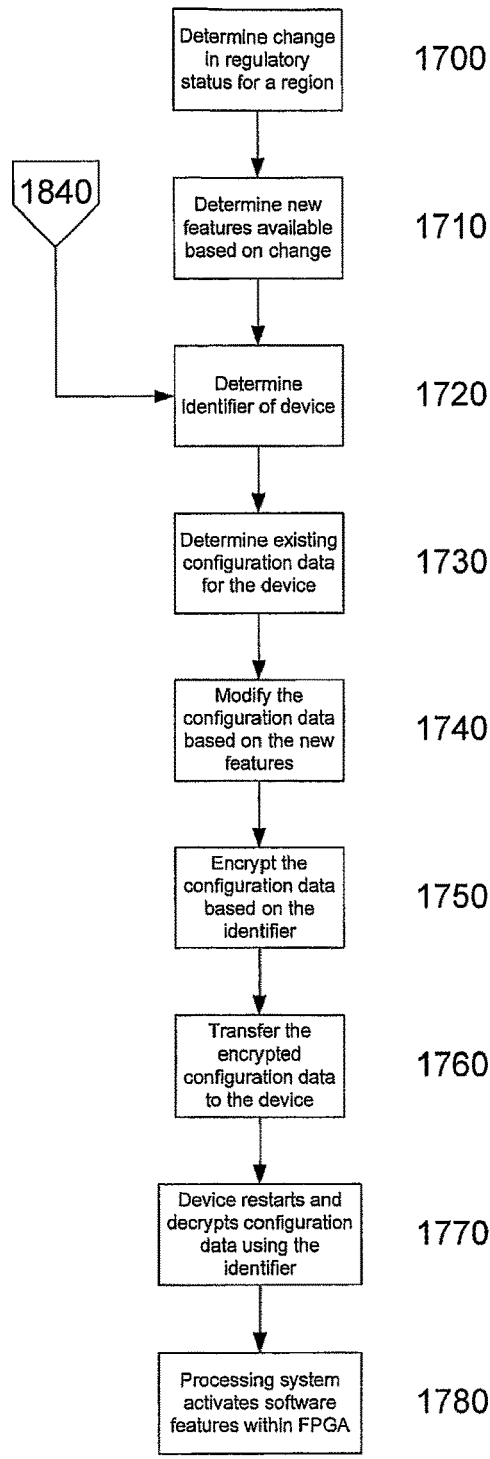
FIG. 17 is a flow chart of a first example of the process of updating a measuring device.

In any event, an example of the process of updating the measuring device 1 will now be described in more detail with reference to FIG. 17. In this example, at step 1700 the base station 1600 determines that there is a change in the regulatory status of features implemented within a certain region. As mentioned above this could occur for example following approval by the TGA of new features.

The base station 1600 uses the change in regulatory status to determine new features available at step 1710, before determining an identifier associated with each measuring device 1 to be updated at step 1720. As changes in regulatory approval are region specific, this is typically achieved by having the base station 1600 access database 1611 including details of the regions in which each measuring device sold are used. The database 1611 includes the identifier for each measuring device 1, thereby allowing the identifier of each measuring device to be updated to be determined.

At step 1730, the base station 1600 determines the existing configuration data, typically from the database 1611, for a next one of the measuring devices 1, before modifying the configuration data to implement the new features at step 1740. The configuration data is then encrypted utilising a key associated with the identifier. The key may be formed from a unique prime number associated with the serial number, or partially derived from the serial number, and is typically stored in the database 1611, or generated each time it is required using a predetermined algorithm.

At step 1760 the encrypted configuration data is transferred to the measuring device 1 as described above.

At step 1770 when the device restarts and the first processing system 10 is activated, the first processing system 10 determines the encryption key, and uses this to decrypt the configuration data. This may be achieved in any one of a number of ways, such as by generating the key using the serial number or other identifier, and a predetermined algorithm. Alternatively, this may be achieved by accessing a key stored in the memory 21. It will be appreciated that any form of encryption may be used, although typically strong encryption is used, in which a secret key is used to both encrypt and decrypt the configuration data, to thereby prevent fraudulent alteration of the configuration by users, as will be explained in more detail below.

At step 1780, the first processing system 10 activates software features within the second processing system 17 using the decrypted configuration data.

It will therefore be appreciated that this provides a mechanism for automatically updating the features available on the measuring device. This may be achieved either by having the second processing system 17 receive new firmware from the processing system 10, or by activating firmware already installed on the second processing system 17, as described above.

As an alternative to performing this automatically when additional features are approved for use, the process can be used to allow features to be activated on payment of a fee. In this example, a user may purchase a measuring device 1 with limited implemented functionality. By payment of a fee, additional features can then be activated as and when required by the user.

Figure 18:
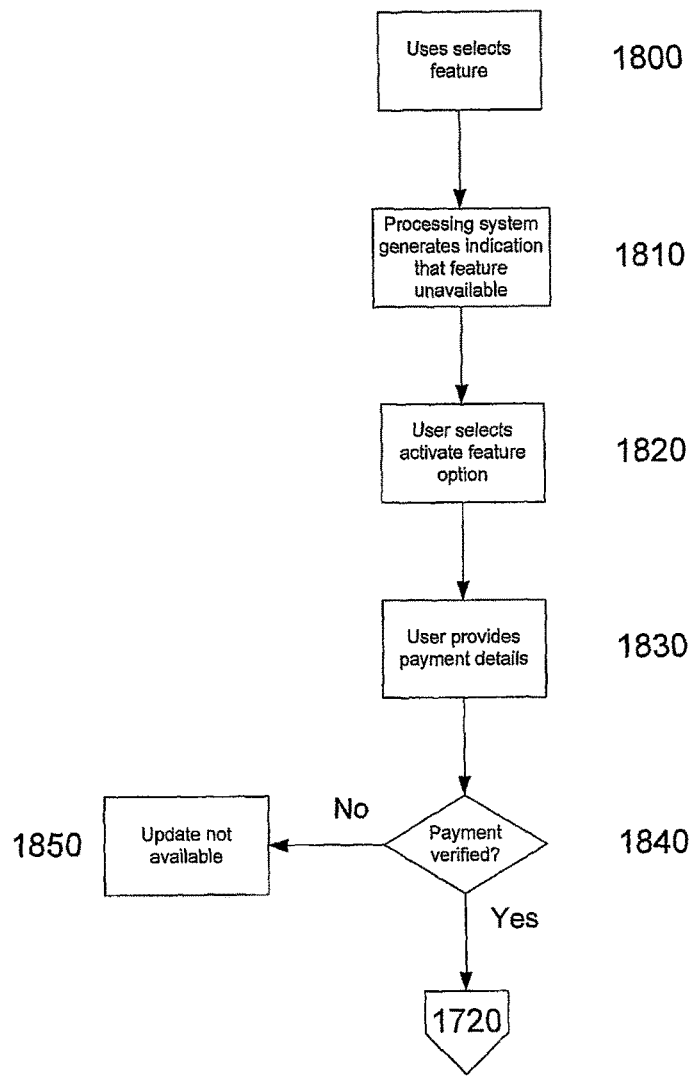
FIG. 18 is a flow chart of a second example of the process of updating a measuring device; and, FIG. 19 is a schematic of an example of a housing configuration for impedance determination apparatus.

In this example, as shown in FIG. 18, when the user selects an inactive feature at step 1800, the first processing system 10 will generate an indication that the feature is unavailable at step 1810. This allows the user to select an activate feature option at step 1820, which typically prompts the user to provide payment details at step 1830. The payment details are provided to the device manufacturer in some manner and may involve having the user phone the device manufacturer, or alternatively enter the details via a suitable payment system provided via the Internet or the like.

At step 1840, once the payment is verified, the process can move to step 1720 to allow an automatic update to be provided in the form of a suitable configuration data. However, if payment details are not verified the process ends at 1850.

It will be appreciated by a person skilled in the art that encrypting the configuration data utilising a unique identifier means that the configuration data received by a measuring device 1 is specific to that measuring device. Accordingly, the first processing system 10 can only interpret the content of a configuration data if it is both encrypted and decrypted utilising the correct key. Accordingly, this prevents users exchanging configuration data, or attempting to re-encrypt a decrypted file for transfer to a different device.

It will be appreciated that in addition to, or as an alternative to simply specifying features in the configuration data, it may be necessary to upload additional firmware to the second processing system 17. This can be used for example, to implement features that could not be implemented using the firmware shipped with the measuring device 1.

In this example, it would be typical for the configuration data to include any required firmware to be uploaded, allowing this to be loaded into the second processing system 17, using the first processing system 10. This firmware can then either be automatically implemented, or implemented in accordance with the list of available features provided in the configuration data.

It will be appreciated that this provides a mechanism for updating and/or selectively activating or deactivating features, such as measuring protocols, impedance analysis algorithms, reports interpreting measured results, or the like. This can be performed to ensure the measuring device conforms to existing TGA or FDA approvals, or the like.

Housing

Figure 19:
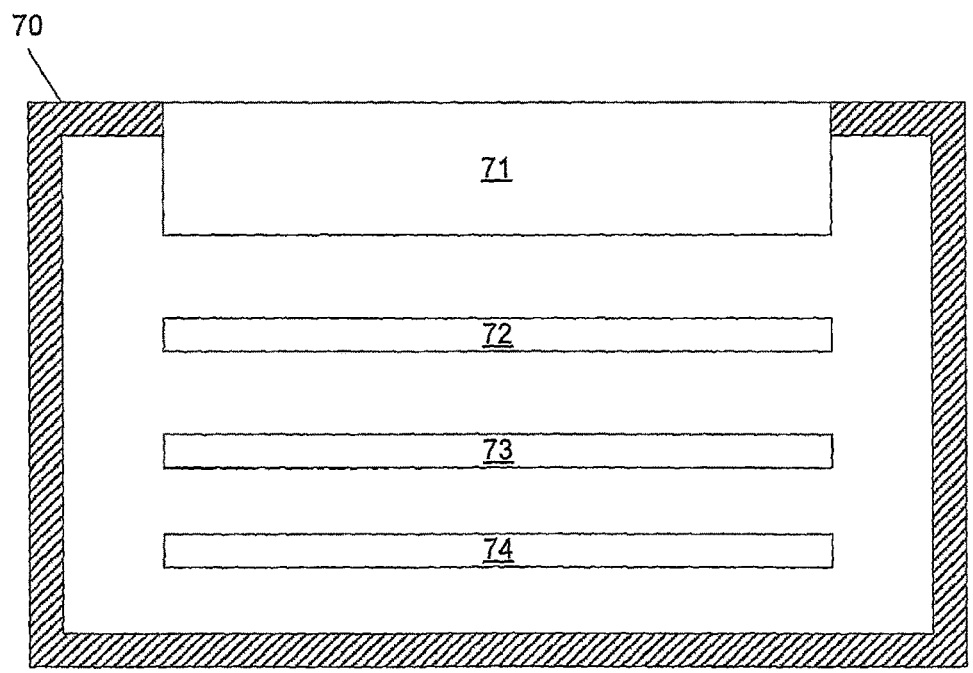

In order to provide a housing configuration with suitable electrical isolation for the subject an arrangement similar to that shown in FIG. 19 can be used.

In this example the measuring device 1 is provided in a housing 70 which includes a touch screen 71, forming the I/O device 22, together with three respective circuit boards 72, 73, 74. In this instance the digital electronics including the second processing system 17 and the first processing system 10 are provided on the circuit board 72. The circuit board 73 is an analogue circuit board and includes the ADCs 37, 38, the DAC 39. A separate power supply board is then provided at 74. The supply board typically includes an integrated battery, allowing the measuring device 1 to form a portable device.

It is also typical housing electrical/magnetic shielding from the external environment, and accordingly, the housing is typically formed from a mu-metal, or from aluminium with added magnesium.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for diagnosing the presence, absence or degree of a range of conditions and illnesses, including, but not limited to oedema, lymphodema, body composition, or the like.

It will also be appreciated above described techniques, such as electrode identification, device updates and the like may be implemented using devices that do not utilise the separate first processing system 10 and second processing system 17, but rather use a single processing system 2, or use some other internal configuration.

Additionally, the end station 1603 can effectively perform any one or more of tasks performed by the first processing system 10 in the examples throughout the specification. Accordingly, the device could be provided without the first processing system 10, with the functionality usually performed by the first processing system 10 being performed by an end station 1603. In this arrangement, the end station 1603 therefore effectively forms part or all of the first processing system 10. This allows the measuring device 1 to be provided including only the second processing system 17 coupled directly to the external interface 23 to allow the measuring device 1 to be controlled by the end station 1603. This would typically be achieved via the use of suitable applications software installed on the end station 1603.

The invention claimed is:

1. A system for performing impedance measurements on a subject, the system comprising:
   a plurality of electrodes configured to be placed in contact with the skin of the subject;
   a signal generator coupled to at least a first subset of the plurality of electrodes;

a sensor coupled to at least a second subset of the plurality of electrodes; and
a first processing system configured to:
receive configuration data from an external system, the configuration data being indicative of at least one feature, the configuration data comprising instructions representing applications software or firmware;
generate control signals to cause the signal generator to generate one or more alternating signals which are applied to the subject via the first subset of the plurality of electrodes;
receive an indication of sensed signals through the subject from the sensor; and
wirelessly communicate information relating to the indication of sensed signals to a second processing system after receiving the indication of sensed signals; and,
a housing, the housing comprising at least the signal generator, the sensor, and the first processing system, and wherein the system is configured to measure and record at least one of: changes in fluid levels, body composition and diagnosis of the presence, absence or degree of at least one of oedema, pulmonary oedema, lymphodema, and cardiac function.

2. The system of claim 1, wherein the second processing system comprises a smart phone.

3. The system of claim 1, wherein the first processing system is configured to perform at least preliminary processing of the indication of sensed signals, and wherein the second processing system is configured to communicate information regarding the processing of the indication of sensed signals to the first processing system.

4. The system of claim 1, wherein the first processing system comprises:
a processor;
a memory; and
an input/output device.

5. The system of claim 1, wherein the first processing system includes programmable hardware, the operation of which is controlled using instructions, and wherein the instructions are stored within inbuilt memory on the first processing system or downloaded from the second processing system.

6. The system of claim 1, wherein the first processing system comprises a Field Programmable Gate Array (FPGA).

7. The system of claim 1, wherein the signal generator includes a current circuit and the sensor includes a voltage circuit, and wherein the system further comprises:
a current ADC configured to:
receive signals from the current circuit; and,
provide the indication of the one or more signals applied to the subject to the first processing system;
a voltage ADC configured to:
receive signals from a voltage circuit; and,
provide the indication of the one or more signals measured from the subject to the first processing system; and
a control signal DAC configured to:
receive the control signals from the first processing system; and,
provide analogue control signals to a current circuit to thereby cause one or more current signals to be applied to the subject in accordance with the control signals.

8. The system of claim 7, further comprising:
at least one buffer circuit configured to:
receive voltage signals from a voltage electrode;
filter and amplify the voltage signals; and,
transfer the filtered and amplified voltage signals to the voltage ADC via a differential amplifier;
at least one current source circuit configured to:
receive one or more control signals;
filter and amplify the control signals to thereby generate one or more current signals;
apply the current signals to a current electrode; and
transfer an indication of the applied signals to the current ADC.

9. The system of claim 8, wherein the first processing system is configured to:
receive signals from the current and voltage ADCs; and
perform preliminary processing of the signals.

10. The system of claim 9, wherein the preliminary processing includes at least one of:
extracting ECG signals; and
filtering the signals.

11. The system of claim 1, wherein the configuration data is indicative of at least one feature and wherein the system is configured to:
determine, using the configuration data, instructions representing the at least one feature; and,
cause, using the instructions, at least one of:
at least one impedance measurement to be performed; and,
at least one impedance measurement to be analysed.

12. The system of claim 11, wherein the second processing system receives configuration data and uses the configuration data to update instructions used by the first processing system.

13. The system of claim 1, wherein the second processing system:
analyses impedance values determined by the first processing system; and
determines one or more biological parameters using the analysis.

14. The system of claim 1, wherein the second processing system:
determines an impedance measurement procedure; and,
at least one of:
analyses impedance measurements in accordance with the impedance measurement procedure; and,
causes the first processing system to perform impedance measurements in accordance with the impedance measurement procedure.

15. The system of claim 14, wherein the second processing system includes a store for storing profiles representing predetermined impedance measurement procedures, the second processing system being coupled to an input device to thereby determine one of the impedance measurement procedures in accordance with input commands from an operator.

16. The system of claim 1, wherein the first processing system:
receives an indication of the one or more signals applied to the subject from the signal generator;
receives an indication of one or more signals measured across the subject from the sensor; and,
performs at least preliminary processing of the indications to thereby allow impedance values to be determined.

17. An apparatus for performing impedance measurements on a subject, the apparatus including:
a signal generator coupled to electrodes configured to be placed on a subject;

a sensor coupled to electrodes configured to be placed on a subject;
a processing system configured to:
perform configuration by:
receiving configuration data from an external system, the configuration data being indicative of at least one feature, the configuration data comprising instructions representing applications software or firmware;
determining, using the configuration data, instructions representing the at least one feature; and,
causing, using the instructions, at least one of:
at least one impedance measurement to be performed; and,
at least one impedance measurement to be analysed; and
perform impedance measurements by:
generating control signals to thereby cause the signal generator to generate one or more alternating signals which are applied to the subject via the drive electrodes;
receiving an indication of sensed signals through the subject from the sensor; and,
determining impedance values at least in part using the indication of the sensed signals.

18. The apparatus of claim 17, wherein the processing system is configured to:
determine an indication of the at least one feature using the configuration data; and,
determine the instructions using the indication of the at least one feature.

19. The apparatus of claim 17, wherein the processing system is configured to decrypt received configuration data.

20. The apparatus of claim 17, wherein the processing system is configured to:
determine a device identifier associated with the measuring device;
determine, using the device identifier, a key; and,
decrypt the received configuration data using the key.

21. The apparatus of claim 17, wherein the processing system is configured to:
receive instructions from a second processing system, the instructions selected using the configuration data; and
generate the control signals using selected instructions.

22. The apparatus of claim 17, wherein the processing system is configured to:
receive instructions from a second processing system; or
access the instructions from a store in response to a communication from a second processing system.

23. The apparatus of claim 17, wherein the processing system receives the configuration data from at least one of a computer system and a communications network.

24. The method of claim 17, wherein receiving configuration data from an external system comprises receiving the configuration data via a wireless connection with an external system.

25. The method of claim 17, wherein receiving configuration data from an external system comprises receiving the configuration data via a wired connection with an external system.

26. A system for performing impedance measurements on a subject, the system including:
a first processing system coupled to a signal generator and a sensor, the signal generator and the sensor being coupled to respective electrodes provided in contact with the subject in use, the first processing system configured to:
receive configuration data from an external system, the configuration data being indicative of at least one feature;
determine, using the configuration data, instructions representing the at least one feature; and
generates control signals which causes the signal generator to generate one or more alternating signals which are applied to the subject via the electrodes, and the sensor configured to determine voltage across or current through the subject, using the electrodes, and transfer appropriate signals to the first processing system; and
a second processing system in wireless communication with the first processing system, the second processing system configured to analyze the impedance values based on an indication of the signals which are applied to the subject and the voltage across or current through the subject, and wherein the system is configured to measure and record at least one of: changes in fluid levels, body composition and diagnosis of the presence, absence or degree of at least one of oedema, pulmonary oedema, lymphodema, and cardiac function.

27. The system of claim 26, wherein the second processing system comprises a smart phone.

28. The system of claim 26, wherein the apparatus is configured to
cause, using the instructions, at least one of:
at least one impedance measurement to be performed; and,
at least one impedance measurement to be analyzed.

29. A system for performing impedance measurements on a subject, the system comprising:
a plurality of electrodes configured to be placed in contact with skin of the subject;
a signal generator coupled to at least a first subset of the plurality of electrodes;
a sensor coupled to at least a second subset of the plurality of electrodes; and
a first processing system configured to:
receive configuration data from an external system, the configuration data being indicative of at least one feature, the configuration data comprising instructions representing applications software or firmware;
generate control signals to cause the signal generator to generate one or more alternating signals which are applied to the subject via the first subset of the plurality of electrodes;
receive an indication of sensed signals through the subject from the sensor; and
communicate information relating to the indication of sensed signals to a second processing system after receiving the indication of sensed signals, the second processing system comprising a smart phone, and wherein the system is configured to measure and record at least one of: changes in fluid levels, body composition and diagnosis of the presence, absence or degree of at least one of oedema, pulmonary oedema, lymphodema, and cardiac function.

30. A system for performing impedance measurements on a subject, the system comprising:
a plurality of electrodes configured to be placed in contact with the skin of the subject;
a signal generator coupled to at least a first subset of the plurality of electrodes;
a sensor coupled to at least a second subset of the plurality of electrodes; and a first processing system configured to:
  receive configuration data from an external system, the configuration data being indicative of at least one feature, the configuration data comprising instructions representing applications software or firmware;
  generate control signals to cause the signal generator to generate one or more alternating signals which are applied to the subject via the first subset of the plurality of electrodes;
  receive an indication of sensed signals through the subject from the sensor; and
  wirelessly communicate information relating to the indication of sensed signals to an external processing system after receiving the indication of sensed signals, wherein the system is configured to measure and record changes in fluid levels.

31. A system for performing impedance measurements on a subject, the system comprising:
  a plurality of electrodes configured to be placed in contact with the skin of the subject;
  a signal generator coupled to at least a first subset of the plurality of electrodes;
  a sensor coupled to at least a second subset of the plurality of electrodes; and
  a first processing system configured to:
    receive configuration data from an external system, the configuration data being indicative of at least one feature, the configuration data comprising instructions representing applications software or firmware;
    generate control signals to cause the signal generator to generate one or more alternating signals which are applied to the subject via the first subset of the plurality of electrodes;
    receive an indication of sensed signals through the subject from the sensor; and
    wirelessly communicate information relating to the indication of sensed signals to an external processing system after receiving the indication of sensed signals, wherein the system is configured to record diagnoses of the presence, absence or degree of at least one of oedema, pulmonary oedema, lymphodema, and cardiac function.

32. A system for performing impedance measurements on a subject, the system comprising:
  a plurality of electrodes configured to be placed in contact with the skin of the subject;
  a signal generator coupled to at least a first subset of the plurality of electrodes;
  a sensor coupled to at least a second subset of the plurality of electrodes; and
  a first processing system configured to:
    receive configuration data from an external system, the configuration data being indicative of at least one feature, the configuration data comprising instructions representing applications software or firmware;
    generate control signals to cause the signal generator to generate one or more alternating signals which are applied to the subject via the first subset of the plurality of electrodes;
    receive an indication of sensed signals through the subject from the sensor; and
    wirelessly communicate information relating to the indication of sensed signals to an external processing system after receiving the indication of sensed signals, wherein the system is configured to measure and record changes in body composition.

* * * * *